United States Patent
Pollack

(10) Patent No.: US 9,470,702 B2
(45) Date of Patent: Oct. 18, 2016

(54) AUTOMATION MAINTENANCE CARRIER AUTO-LOADER

(71) Applicant: Benjamin S. Pollack, Budd Lake, NJ (US)

(72) Inventor: Benjamin S. Pollack, Budd Lake, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 14/434,594

(22) PCT Filed: Oct. 11, 2013

(86) PCT No.: PCT/US2013/064635
§ 371 (c)(1),
(2) Date: Apr. 9, 2015

(87) PCT Pub. No.: WO2014/059335
PCT Pub. Date: Apr. 17, 2014

(65) Prior Publication Data
US 2015/0241458 A1    Aug. 27, 2015

Related U.S. Application Data

(60) Provisional application No. 61/712,694, filed on Oct. 11, 2012.

(51) Int. Cl.
G01N 35/04 (2006.01)
B65G 21/16 (2006.01)
G01N 35/00 (2006.01)

(52) U.S. Cl.
CPC ............... *G01N 35/04* (2013.01); *B65G 21/16* (2013.01); *G01N 35/00623* (2013.01); *G01N 35/00732* (2013.01); *G01N 35/00871* (2013.01); *G01N 35/00693* (2013.01); *G01N 2035/00851* (2013.01); *G01N 2035/0465* (2013.01); *G01N 2035/0467* (2013.01); *G01N 2035/0493* (2013.01)

(58) Field of Classification Search
CPC .......... G01N 35/04; G01N 35/00871; G01N 35/00732; G01N 35/00623; G01N 35/00693; G01N 2035/00851; G01N 2035/0493; G01N 2035/0467; G01N 2035/0465; B65H 21/16
See application file for complete search history.

(56) References Cited

U.S. PATENT DOCUMENTS

| | | | | |
|---|---|---|---|---|
| 4,986,715 | A | * 1/1991 | Asakawa | H01L 21/67769 211/163 |
| 2005/0011725 | A1 | * 1/2005 | Lapeyre | B65G 47/844 198/370.02 |
| 2008/0209709 | A1 | * 9/2008 | Mayer | B01D 61/18 29/426.5 |
| 2009/0003981 | A1 | * 1/2009 | Miller | B65G 1/04 414/267 |

OTHER PUBLICATIONS

PCT International Search Report and Written Opinion dated Mar. 7, 2014 (16 Pages).

* cited by examiner

*Primary Examiner* — Patrick Cicchino

(57) ABSTRACT

Devices and systems are provided for automatically deploying maintenance carriers to an automation track. These maintenance carriers can include tools appropriate for providing a maintenance operation, such as cleaning a track, aligning a pipette, and inspecting portions of the automation system. An auto-loader can be provided to selectively deploy and/or retrieve maintenance carriers and provide recharging, refilling, or disposal of carriers or cartridges used by the maintenance carriers.

18 Claims, 21 Drawing Sheets

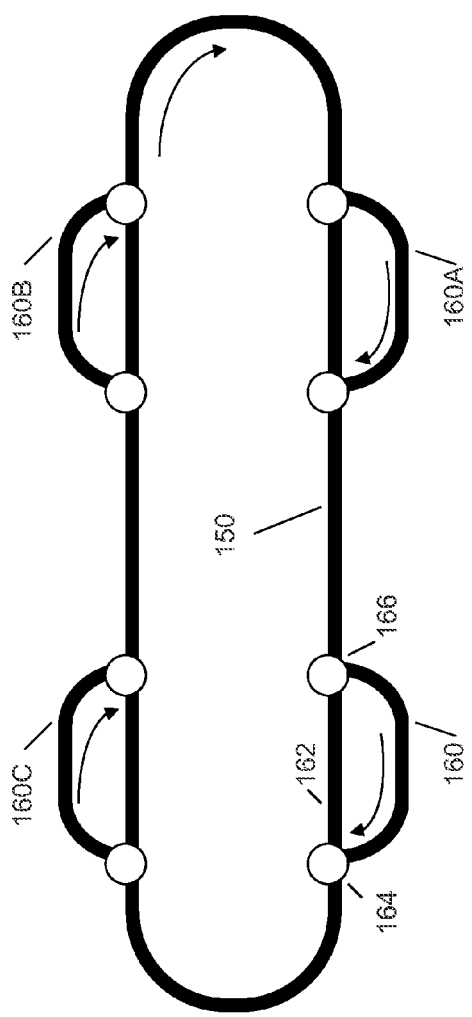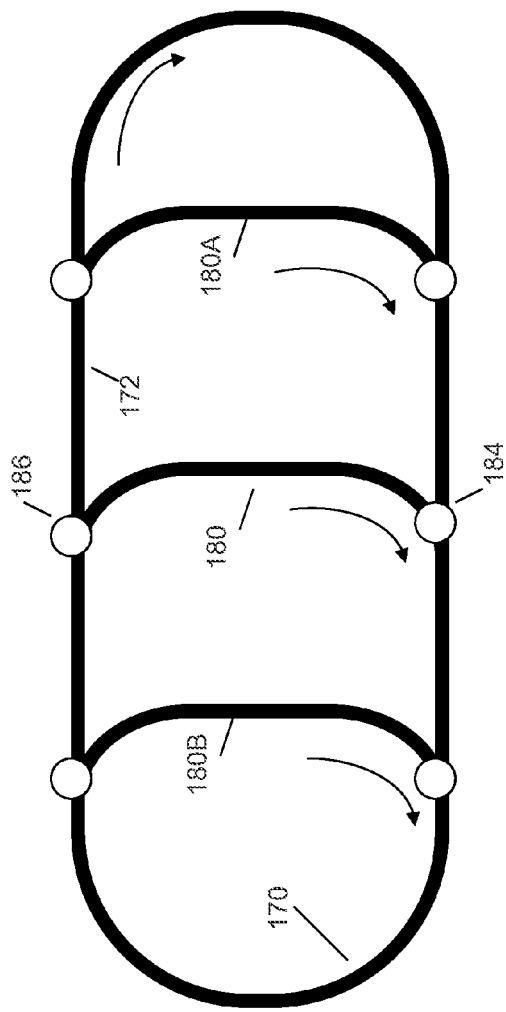

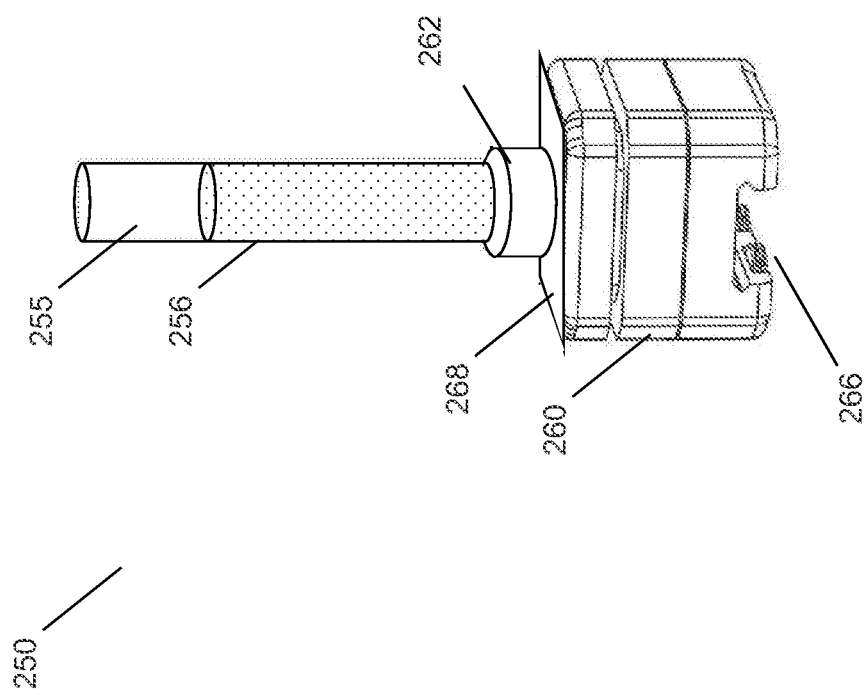

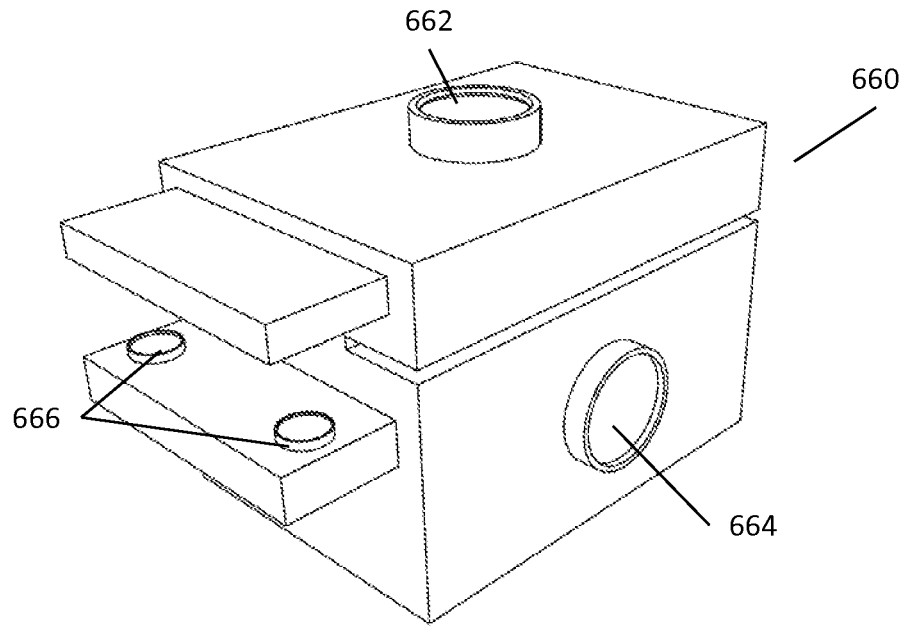
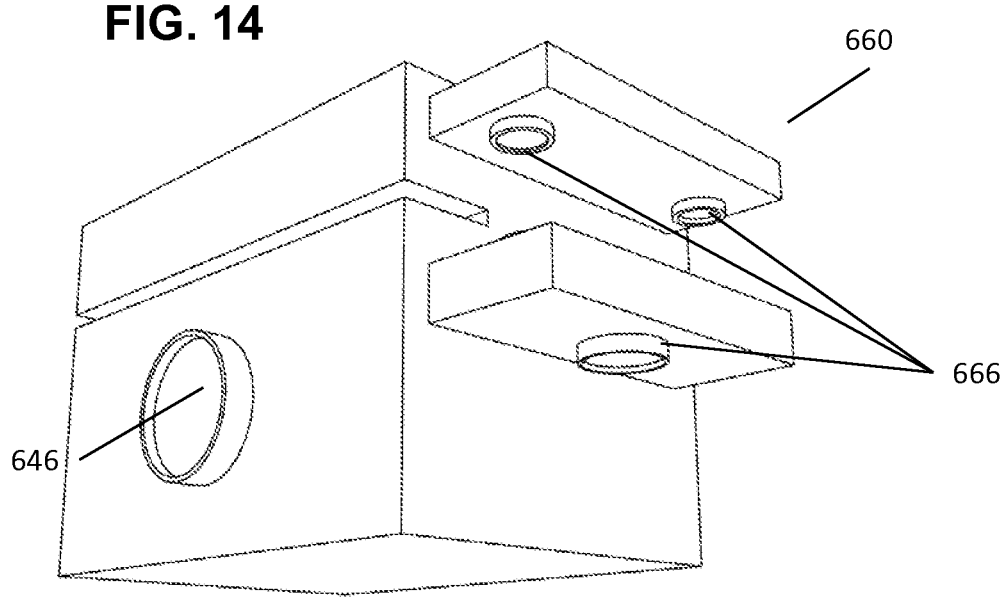
FIG. 14

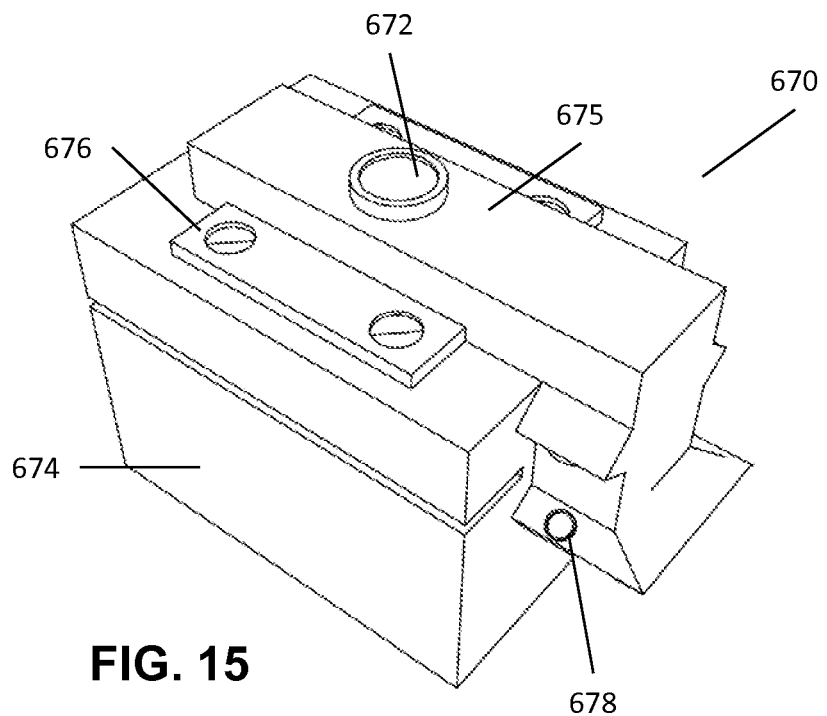
FIG. 15
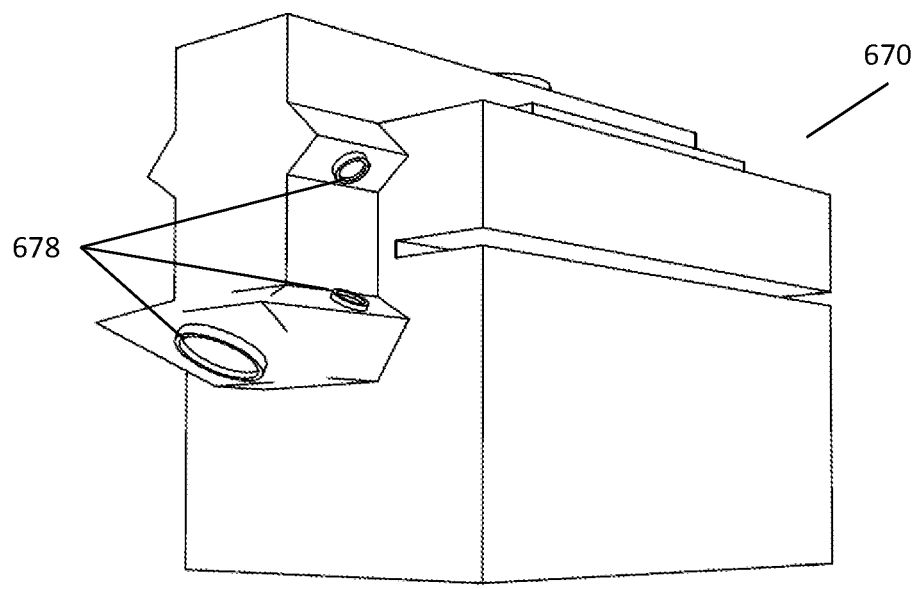

AUTOMATION MAINTENANCE CARRIER AUTO-LOADER

CROSS-REFERENCE TO RELATED APPLICATIONS

This application claims priority to U.S. provisional application Ser. No. 61/712,694 filed Oct. 11, 2012, which is incorporated herein by reference in its entirety.

TECHNOLOGY FIELD

The present invention relates in general to an automation system for use in a laboratory environment and, more particularly, to systems and methods for maintaining an automation system for in a clinical analyzer. Embodiments of the present invention are particularly well suited, but in no way limited, to independently movable maintenance carriers.

BACKGROUND

In-vitro diagnostics (IVD) allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers (analyzers) onto which fluid containers, such as tubes or vials containing patient samples, have been loaded. The analyzer extracts a liquid sample from the vial and combines the sample with various reagents in special reaction cuvettes or tubes (referred to generally as reaction vessels). In some conventional systems, a modular approach is used for analyzers. A lab automation system can shuttle samples between one sample processing (module) and another module. Modules may include one or more stations, including sample handling stations and testing stations (e.g., a unit that can specialize in certain types of assays or can otherwise provide testing services to the larger analyzer), which may include immunoassay (IA) and clinical chemistry stations. Some traditional IVD automation track systems comprise systems that are designed to transport samples from one fully independent module to another standalone module. This allows different types of tests to be specialized in two different stations or allows two redundant stations to be linked to increase the volume of sample throughput available. These lab automation systems, however, are often bottlenecks in multi-station analyzers. Relatively speaking, traditional lab automation systems lack large degrees of intelligence or autonomy to allow samples to independently move between stations.

In an exemplary prior art system, a friction track, much like a conveyor belt, shuttles individual carrier mechanisms, sometimes called pucks, or racks of containers between different stations. Samples may be stored in sample containers, such as test tubes that are placed into a puck by an operator or robot arm for transport between stations in an analyzer along the track. Automation systems are inherently complex mechanical systems, often having moving parts and surfaces that interact with carriers. The automation system may also include instruments, such as pipettes or robot arms that interact with samples or sample carriers. Due to the complex nature of these systems, failures of systems can occur that affect the reliability of the automation system. Failures may result in down time of the analyzer or analyzer stations that prevent further sample analysis until a repair technician can fix the problem. Many failures are preventable with proper maintenance. However, prior art systems either forego most maintenance operations or make maintenance a difficult manual task. Accordingly, many prior are systems suffer downtime from preventable failures that may have been mitigated had maintenance been a more viable option for operators.

SUMMARY

Embodiments of the present invention address and overcome one or more of the above shortcomings and drawbacks by providing devices and systems for automatically deploying maintenance carriers to an automation track. These maintenance carriers can include tools appropriate for providing a maintenance operation, such as cleaning a track, aligning a pipette, inspection portions of the automation system. An auto-loader can be provided to selectively deploy and/or retrieve maintenance carriers and provide recharging, refilling, or disposal of carriers or cartridges used by the maintenance carriers.

According to one embodiment of the invention, an automation system includes a track, a plurality of maintenance carriers, and an auto-loader for selectively deploying one or more or the plurality of maintenance carriers on the track. In one aspect, the automation system can include a plurality of sample carriers that traverse the track. In another aspect, the auto-loader can include a robot arm. In yet another aspect, the plurality of maintenance carriers can include a plurality of types of maintenance carriers. In a further aspect, the auto-loader can select a maintenance carrier in response to a detected condition of the track. In still another aspect, a storage rack can store the plurality of maintenance carriers. The storage rack can be configured to recharge the plurality of maintenance carriers. In an additional aspect, the auto-loader can be configured to install a maintenance cartridge in one or more of the plurality of maintenance carriers. In another aspect, the auto-loader can be configured to replenish a fluid in one or more of the plurality of maintenance carriers.

According to another embodiment of the invention, a method for performing maintenance to an analyzer includes the steps of determining a maintenance operation to perform, automatically selecting a maintenance carrier to perform the maintenance operation, and under the control of a processor, automatically deploying the maintenance carrier onto a track. The method further includes performing the maintenance operation using the maintenance carrier, and returning the maintenance carrier to a storage or waste location.

In one aspect, the step of determining a maintenance operation to perform can occur in response to an explicit request by an operator. In another aspect, the step of determining a maintenance operation to perform can occur in response to detecting an error. In another aspect, the step of determining a maintenance operation to perform can occur at a prescheduled time. In yet another aspect, the method further determines a status of a fluid in the maintenance carrier. In still another aspect, the method can include refilling the at least fluid in the maintenance carrier if the fluid level is low. In a further aspect, the method can include replacing a maintenance cartridge in the maintenance carrier if the fluid level is low or recharging the maintenance carrier when it is in the storage location. In another aspect, the method can monitor at least one status of the maintenance carrier and reporting that status to an operator. In a further aspect, the maintenance carrier can be selected from a plurality of maintenance carriers in the storage location.

According to another embodiment of the invention, auto-loader for use with an automation system includes a storage area configured to hold a plurality of maintenance carrier and a robot arm configured to selectively load and unload the at least one of the maintenance carriers with respect to at least one automation track. The robot arm is further configured to move the at least one of the maintenance carriers responsive to a processor in communication with an analyzer.

In one aspect, the storage area is configured to recharge at least one of the maintenance carriers or install a maintenance cartridge in one or more of the plurality of maintenance carriers.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIGS. 2A and 2B are diagrammatic views of track geometries that can be used with the automation system embodiments disclosed herein;

FIG. 4A is a perspective view of an exemplary carrier that can be used with the embodiments disclosed herein;

FIG. 14 is a multi-angle perspective view of an inspection maintenance carrier for use with certain embodiments;

FIG. 15 is a multi-angle perspective view of an inspection maintenance carrier for use with certain embodiments;

DETAILED DESCRIPTION OF ILLUSTRATIVE EMBODIMENTS

Figure 1:
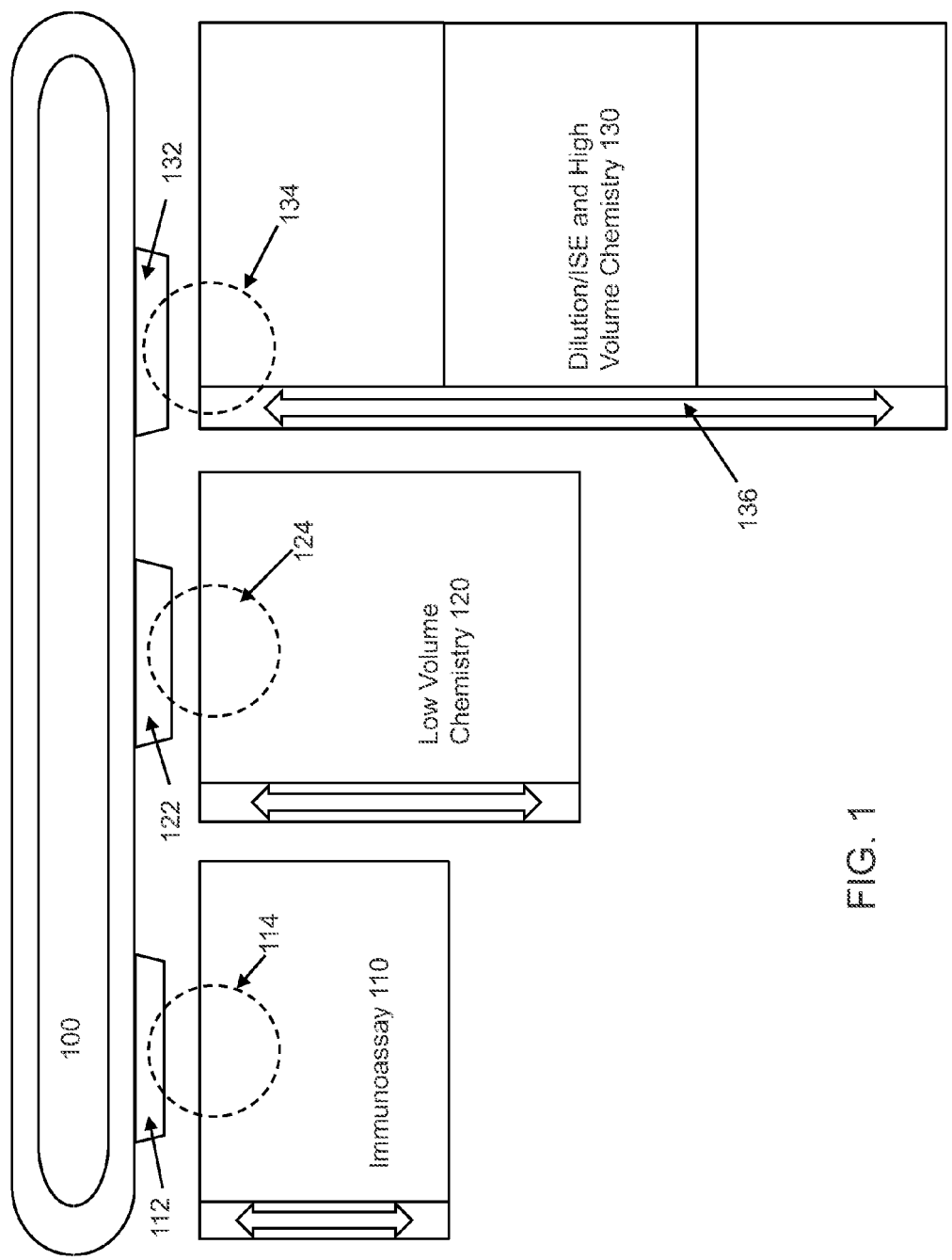
FIG. 1 is a top view of an exemplary clinical chemistry analyzer geometry that can be improved by use of the automation system embodiments disclosed.

Terms and Concepts Associated with Some Embodiments

Analyzer: Automated clinical analyzers ("analyzers") include clinical chemistry analyzers, automated immunoassay analyzers, or any other type of in vitro diagnostics (IVD) testing analyzers. Generally, an analyzer performs a series of automated IVD tests on a plurality of patient samples. Patient samples may be loaded into an analyzer (manually or via an automation system), which can then perform one or more immunoassays, chemistry tests, or other observable tests on each sample. The term analyzer may refer to, but is not limited to, an analyzer that is configured as a modular analytical system. A modular analytical system includes an integrated and extendable system comprising any combinations of a plurality of modules (which can include the same type of module or different types of modules) interconnected in a linear or other geometric configuration by an automation surface, such as an automation track. In some embodiments, the automation track may be configured as an integral conveyance system on which independent carriers are used to move patient samples and other types of material between the modules. Generally, at least one module in a modular analytical system is an analyzer module. Modules may be specialized or made redundant to allow higher throughput of analytical tasks on patient samples.

Analyzer module: An analyzer module is a module within a modular analyzer that is configured to perform IVD tests, such as immunoassays, chemistry tests, or other observable tests on patient samples. Typically, an analyzer module extracts a liquid sample from a sample vessel and combines the sample with reagents in reaction cuvettes or tubes (referred to generally as reaction vessels). Tests available in an analyzer module may include, but are not limited to, a subset of electrolyte, renal or liver function, metabolic, cardiac, mineral, blood disorder, drug, immunoassay, or other tests. In some systems, analyzer modules may be specialized or made redundant to allow higher throughput. The functions of an analyzer module may also be performed by standalone analyzers that do not utilize a modular approach.

Carrier: A carrier is a transportation unit that can be used to move sample vessels (and, by extension, fluid samples) or other items in an automation system. In some embodiments, carriers may be simple, like traditional automation pucks (e.g., passive devices comprising a holder for engaging a tube or item, a friction surface to allow an external conveyor belt in the automation track to provide motive force, and a plurality of sides that allow the puck to be guided by walls or rails in the automation track to allow the track to route a puck to its destination). In some embodiments, carriers may include active components, such as processors, motion systems, guidance systems, sensors, and the like. In some embodiments, carriers can include onboard intelligence that allows carriers to be self-guided between points in an automation system. In some embodiments, carriers can include onboard components that provide motive forces while, in others, motive forces may be provided by an automation surface, such as a track. In some embodiments, carriers move along automation tracks that restrict motion to a single direction (e.g., fore and aft) between decision points. Carriers may be specialized to a given payload in an IVD environment, such as having a tube holder to engage and carry a sample tube, or may include mounting surfaces suitable to carry different items around an automation system. Carriers can be configured to include one or more slots (e.g., a carrier may hold one or a plurality of sample vessels).

Central controller or processor: A central controller/processor (which may sometimes be referred to as a central scheduler) is a processor that is part of the automation system, separate from any processors onboard carriers. A central controller can facilitate traffic direction, scheduling, and task management for carriers. In some embodiments, a central controller can communicate with subsystems in the automation system and wirelessly communicate with carriers. This may also include sending trajectory or navigational information or instructions to carriers and determining which carriers should go where and when. In some embodiments, local processors may be responsible for managing carriers on local track sections, such as managing local queues. These local processors may act as local equivalents to central controllers.

Decision point: Decision points are points on an automation track where different navigational or trajectory decisions may be made for different carriers. A common example includes a fork in a track. One carrier may proceed without turning, while another may slow down and turn. Decision points may include stopping points at instruments, where some carriers may stop, while others may proceed. In some embodiments, deceleration zones ahead of turns may act as decision points, allowing carriers that will be turning to slow down to limit lateral forces, while others may proceed if not turning or if the motion profile for that carrier does not require slowing down. The decisions made at decision points can be made by processors onboard carriers, processors local to the track section, a central processor, or any combination thereof, depending on the embodiment.

Independent carrier: In some embodiments, carriers may be characterized as independently controlled carriers. Independently controlled carriers are carriers with independently controlled trajectories. In some embodiments, independent carriers may be operating at the same time, on the same track, with carriers carrying one or a plurality of combinations of payloads that differ by size, weight, form factor, and/or content. The trajectories of each independently controlled carrier may be limited by a motion profile that includes; maximum jerk, acceleration, direction, and/or speed for the carrier while moving in the automation system. The motion profile can limit or define the trajectory for each carrier independently. In some embodiments, a motion profile can be different for different sections of the automation system (e.g., in straight track sections vs. around curves to account for the added lateral forces while turning), for different carrier states (e.g., an empty carrier may have a different motion profile from a carrier transporting a sample or from a carrier transporting a reagent or other item), and/or for different carriers. In some embodiments, carriers can include onboard propulsion components that allow individual carriers to independently operate responsive to a motion profile or trajectory or destination instructions intended for each separate carrier.

Intelligent carrier/semi-autonomous carriers: In some embodiments, carriers may be characterized as intelligent carriers. An intelligent carrier is a carrier with onboard circuits that participates in motion, routing, or trajectory decisions. An intelligent carrier can include digital processors that execute software instructions to proceed along an automation surface responsive to the instructions or onboard analog circuits that respond to motion input (e.g., line follower circuits). Instructions may include instructions characterizing motion profiles, traffic, or trajectory rules. Some intelligent carriers may also include onboard sensors to assist onboard processors to route the carrier or make decisions responsive to the carrier's environment. Some intelligent carriers may include onboard components, such as motors or magnets, which allow the carrier to move responsive to control of an onboard processor.

In vitro diagnostics (IVD): In vitro diagnostics (IVD) are tests that can detect diseases, conditions, infections, metabolic markers, or quantify various constituents of bodily materials/fluids. These tests are performed in laboratory, hospital, physician office, or other health professional settings, outside the body of a patient. IVD testing generally utilizes medical devices intended to perform diagnoses from assays in a test tube or other sample vessel or, more generally, in a controlled environment outside a living organism. IVD includes testing and diagnosis of disease or quantifying various constituents of bodily materials/fluids based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with analyzers into which tubes or vials containing patient samples have been loaded. IVD can refer to any subset of the IVD functionality described herein.

Landmarks: In embodiments where carriers include onboard sensors, optical or other marks in track surfaces or locations viewable/sensible from track surfaces can act as landmarks. Landmarks can convey geographic information to carriers, such as a current location, upcoming stopping location, decision point, turn, acceleration/deceleration points, and the like.

Lab automation system: Lab automation systems include any systems that can automatically (e.g., at the request of an operator or software) shuttle sample vessels or other items within a laboratory environment. With respect to analyzers, an automation system may automatically move vessels or other items to, from, amongst, or between stations in an analyzer. These stations may include, but are not limited to, modular testing stations (e.g., a unit that can specialize in certain types of assays or can otherwise provide testing services to the larger analyzer), sample handling stations, storage stations, or work cells.

Module: A module performs specific task(s) or function(s) within a modular analytical system. Examples of modules may include: a pre-analytic module, which prepares a sample for analytic testing, (e.g., a decapper module, which removes a cap on top of a sample test tube); an analyzer module, which extracts a portion of a sample and performs tests or assays; a post-analytic module, which prepares a sample for storage after analytic testing (e.g., a recapper module, which reseals a sample test tube); or a sample handling module. The function of a sample handling module may include managing sample containers/vessels for the purposes of inventory management, sorting, moving them onto or off of an automation track (which may include an integral conveyance system, moving sample containers/vessels onto or off of a separate laboratory automation track, and moving sample containers/vessels into or out of trays, racks, carriers, pucks, and/or storage locations.

Payload: While exemplary carriers are described with respect to carrying patient samples, in some embodiments, carriers can be used to transport any other reasonable payload across an automation system. This may include fluids, fluid containers, reagents, waste, disposable items, parts, or any other suitable payloads.

Processor: A processor may refer to one or more processors and/or related software and processing circuits. This may include single or multicore processors, single or multiple processors, embedded systems, or distributed processing architectures, as appropriate, for implementing the recited processing function in each embodiment.

Pullouts, sidecars, offshoot paths: These terms may be used to refer to track sections that are off the main portion of a track system. Pullouts or sidecars may include chords, parallel tracks, or other suitable means for separating some carriers from a primary traffic pattern. Pullouts or sidecars may be configured to facilitate physical queues or allow certain carriers to stop or slow down without disrupting traffic on a main track section.

Samples: Samples refers to fluid or other samples taken from a patient (human or animal) and may include blood, urine, hematocrit, amniotic fluid, or any other fluid suitable for performing assays or tests upon. Samples may sometimes refer to calibration fluids or other fluids used to assist an analyzer in processing other patient samples.

STAT (short turnaround time) sample: Samples may have different priority assigned by a laboratory information system (LIS) or operator to assign STAT priority to samples that should take precedent over non-STAT samples in the analyzer. When used judiciously, this may allow certain samples to move through the testing process faster than other samples, allowing physicians or other practitioners to receive testing results quickly.

Station: A station includes a portion of a module that performs a specific task within a module. For example, the pipetting station associated with an analyzer module may be used to pipette sample fluid out of sample containers/vessels being carried by carriers on an integrated conveyance system or a laboratory automation system. Each module can include one or more stations that add functionality to a module.

Station/module: A station includes a portion of an analyzer that performs a specific task within an analyzer. For example, a capper/decapper station may remove and replace caps from sample vessels; a testing station can extract a portion of a sample and perform tests or assays; a sample handling station can manage sample vessels, moving them onto or off of an automation track, and moving sample vessels into or out of storage locations or trays. Stations may be modular, allowing stations to be added to a larger analyzer. Each module can include one or more stations that add functionality to an analyzer, which may be comprised of one or more modules. In some embodiments, modules may include portions of, or be separate from, an automation system that may link a plurality of modules and/or stations. Stations may include one or more instruments for performing a specific task (e.g., a pipette is an instrument that may be used at an immunoassay station to interact with samples on an automation track). Except where noted otherwise, the concepts of module and station may be referred to interchangeably.

Tubes/sample vessels/fluid containers: Samples may be carried in vessels, such as test tubes or other suitable vessels, to allow carriers to transport samples without contaminating the carrier surfaces.

EXEMPLARY EMBODIMENTS

The above problems in the prior art have motivated the discovery of improved apparatus and methods for providing automated maintenance capabilities to an automation system. In addition to a plurality of carriers that transport samples between and amongst stations in an automated clinical analyzer ("analyzer"), maintenance carriers can be provided that include tools suitable to perform a maintenance function. These maintenance carriers can traverse the automation system along with sample carriers, allowing them access to locations that may be difficult for a human to reach and can provide maintenance to any suitable portion (or the whole) of the automation system. Maintenance operations can include, but are not limited to: cleaning the track and components of the analyzer (such as pipettes), calibrating the analyzer, aligning components (such as pipettes), inspecting the condition of the automation system and the systems of the analyzer, and replacing disposable/serviceable components such as pipette tips and robot arm effector pads. In some embodiments, maintenance carriers can be remotely controlled over a network to provide remote inspection of the analyzer by off-site personnel.

Embodiments of the present invention can also utilize an auto-loader to selectively deploy maintenance carriers automatically and/or on-demand. The auto-loader can allow maintenance carriers to be loaded onto and unloaded from an automation track to participate in maintenance actions. In some embodiments, the auto-loader acts as storage for the maintenance carriers when not in use, as well as a recharge and refill station to recharge any batteries and refill any fluids that may be used in some embodiments of the maintenance carriers.

An exemplary track geometry for use in transporting samples within an analyzer, typical in prior art configurations, is shown in FIG. 1. This track can include prior art friction tracks, which may introduce problems in designing a track system. However, certain embodiments of the present invention could also use a similar geometry without necessarily employing a friction track for motion. Track 100 can be a generally oval-shaped track that conveys samples in pucks or trays between various stations, such as sample preparation or analyzing/testing stations 110, 120, and 130. Track 100 could be a single direction track or, in some instances, a linear bidirectional track. In this exemplary set-up, each analyzer 110, 120, 130 is serviced by a respective sidecar 112, 122, 132. At the junction between the track 100 and each sidecar, a gate or switch can be placed that allows samples to be diverted to or from track 100 to the sidecar. The oval nature of track 100 can be used to circulate samples while they wait for access to each analyzer. For example, analyzer 110 may have a full queue in sidecar 112, such that new samples on track 100 cannot be diverted to sidecar 112 until analyzer 110 finishes handling a pending sample in sidecar 112 and inserts it back into the main traffic flow of track 100.

In some prior art systems, each sidecar can be serviced by a handling mechanism such as sample probe arms 114, 124, and 134. These robotic handling arms can aspirate sample material from samples in a sidecar via a probe needle, or can pick up a sample tube from the sidecar and transport it into the corresponding testing station. In this exemplary system, the available testing stations include an immunoassay station 110, a low-volume chemistry station 120, and an expandable dilution/ISE electrolyte and high-volume chemistry station or stations 130. Some advantages of this approach are that the track 100 can be part of a separate lab automation system that can be added onto otherwise self-contained stations, and the track 100 and stations 110, 120, and 130 can be independently upgraded, purchased, or serviced. Some stations, such as high-volume chemistry station 130, can include their own friction track 136 that operates independently of track 100. Friction track 136 can include a bidirectional friction track that allows samples to move between sub-modules of high-volume chemistry station 130. A drawback of this type of system is that the separate friction tracks operate independently and, control of overall automation becomes more complicated. Furthermore, transitions between friction tracks 136 and 100 can be slow and cumbersome, particularly where there is no direct route between two friction tracks. In some systems, moving between tracks may require lifting and placing samples via a robot arm.

Prior art lab automation systems for analyzers generally treat individual analyzer/testing stations as generic destinations for a sample on the track. In some embodiments of the present invention, the lab automation system can be integrated within the individual testing stations, which can substantially reduce or eliminate the complexity of the individual testing stations and reduce the need for separate sample handling systems within each station. In some embodiments, by integrating the lab automation system into the stations, the system can begin to treat individual stations less as generic destinations and more as portions of a multi-route track onto which a sample can travel.

FIG. 2A shows one embodiment of a track system that can be adapted for use with the present invention. Track 150 is a rectangular/oval/circular track on which sample carriers move in a clockwise (or counterclockwise) direction. Track 150 may be unidirectional or bidirectional. Carriers can transport any suitable payload with an IVD environment, such as fluid samples, reagents, or waste. Fluids, such as patient samples can be placed in a container or vessel, such as a test tube, vial, cuvette, etc. that can be transported by a carrier. Carrier, as used herein, is a general term for pucks, trays, or the like for handling material in accordance with the disclosed embodiments. Carriers and, by extension, payloads such as samples, can move on the main track 150 or be diverted via decision points such as 164 or 166. These decision points can be mechanical gates (as in the prior art) or other mechanisms suitable for allowing a sample to be diverted from the main track 150 to a sidecar, such as 160, 160A, 160B, 160C as described herein. By way of example, if a sample carrier is traversing the main path 150 and reaches decision point 166, it can be made to continue on the main track to segment 162 or it can be made to divert to sidecar 160. The systems and methods by which the decision can be made to divert the sample carrier at decision point 166 are described throughout.

FIG. 2B shows an alternative track layout that may be suitable for certain embodiments of the present invention. Track 170 is also a generally circular track with sample carriers moving clockwise (or counterclockwise). In this example, rather than having sidecars outside of the track, pullouts 180, 180A, and 180B are chords within the track. Similarly, when sample carriers reach decision points, they may be diverted off of the main path to a side path such as path 180. At decision point 186, a sample on the main track 170 can be made to continue on the main track on segment 172 or be diverted onto path 180. Once an analyzer station along handling path 180 is done processing the sample, the sample proceeds to decision point 184 where it may be placed back onto the main path 170.

Figure 3:
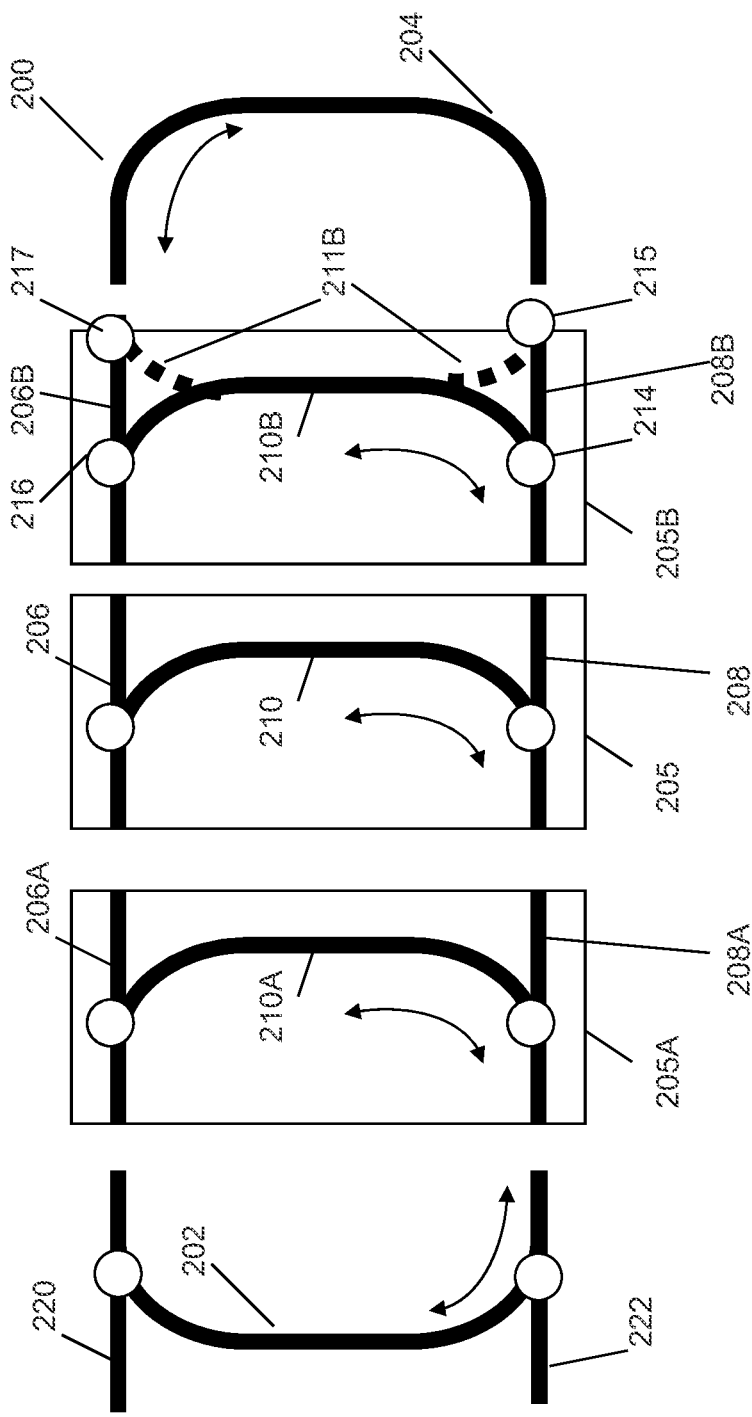
FIG. 3 is a diagrammatic view of an exemplary modular track configuration that can be used with the embodiments disclosed herein.

FIG. 3 shows a modular approach to the automation system track that can be used for certain embodiments of the present invention. In this example, the tracks may be integrated into individual analyzer stations, such that the track can be used as part of the internal motion or sample handling system of individual lab stations. In the prior art, it is common to have multiple different types of motion systems within different analyzer/testing stations. For example, some stations can include friction tracks for shuttling pucks or trays of sample tubes, and may include carousels containing smaller vessels, such as cuvettes and reaction vessels, into which portions of the sample can be aspirated and dispensed. In some embodiments, by integrating portions of the track system into the analyzer stations themselves, each station can include its own queuing logic and may be simplified to eliminate unnecessary internal motion systems.

With respect to FIG. 3, the track 200 can be broken into modular components that are integrated into analyzer modules. In this exemplary track, modules 205, 205A, and 205B can be combined with one another and optionally other modular track components 202 and 204 to form a track similar to that shown in FIG. 2B. For instance, 205A can be a module that performs the same function as immunoassay 110 (FIG. 1), 205 can be a module that performs the same function as low-volume chemistry module 120 (FIG. 1), and 205B can be a module that performs ISE electrolyte testing, like module 130 (FIG. 1). In this example, the main outer track can be formed by track segments 202, 204, 206, 206A, 206B, 208, 208A, and 208B. Within the analyzer modules 205, 205A, and 205B, internal paths 210, 210A, and 210B form pullouts from the main track. The internal paths can be used for internal queuing and can be managed independently within each analyzer module to allow each module to have greater control over samples to be processed.

One advantage of integrating track 200 and sub-paths 210, 210A, and 210B into the analyzer modules 205, 205A, and 205B, respectively, is that the internal handling mechanisms within each analyzer module can be specially adapted to better coordinate with the track sub-paths. In some embodiments, modules 205, 205A, and 205B can be adapted to process each sample within a period that is less than an operation cycle of the overall analyzer, leaving enough time for the sample to be routed along the track system to another module after processing, allowing the other module to immediately process the sample on the next operation cycle. As used herein, an operation cycle is a unit of time used by scheduling algorithms to allot processing time to modules for sample assays. These can be dynamic or fixed and can allow synchronous operation of the modules in the analyzer and provide a reliable timing model for scheduling samples amongst multiple modules in the analyzer. The operation cycle time can be chosen to be the time needed by any given module between when it starts processing a first sample, and when it is ready to process another sample under expected steady-state conditions. For example, if an analyzer can process one test every three seconds, and the expected average tests per sample is seven, the operation cycle time can be 21 seconds. It should be understood that individual modules can implement efficiency techniques, such as parallelism or processing multiple samples within a cycle, to maximize throughput, even when the number of tests-per-sample varies from an expected amount. Furthermore, it should be understood that in some embodiments, individual modules have different operation cycle times, and these modules can operate substantially asynchronously from one another. Virtual queues or buffers can be used to assist the management of sample scheduling where cycle times or demand vary between modules.

Enabling transit between modules in the analyzer in a reliable time frame, on the order of a single operation cycle or less, achieves many performance advantages not possible with prior art track systems. If a sample can be reliably handled by an analyzer module and transported to the next analyzer module within a single cycle of the analyzer, traffic handling in queuing becomes much simpler, throughput becomes more consistent, and latency can be controlled and reduced. Essentially, in such an analyzer, a sample can reliably be handled by the track system and processed uniformly such that a sample does not sit idly on the track system waiting in queues. Furthermore, queues within the system, such as queues within a given analyzer module, can reliably be shortened, limited by the number of modules within the system.

In some embodiments of the present invention, the reliable and rapid nature of the track system enables queues to be virtual, rather than physical. A virtual queue can be handled in software, rather than by physical limitations. Traditionally, queues have been physical. The simplest physical queue is effectively a traffic jam at any given part of a sample handling operation. A bottleneck creates a first-in first-out (FIFO) queue, where sample carriers are effectively stopped in a line, providing a buffer so that an analyzer or a decision point can request the next sample in the queue when it is ready. Most prior art lab automation tracks maintain FIFO processing queues to buffer samples that are waiting to be processed by the attached modules (analyzers or pre/post analytic devices). These buffers allow the track to process sample tubes at a constant rate, even though the modules or operator requests can create bursts of demand. FIFO queues can also substantially increase the throughput of the individual modules by allowing them to perform preprocessing tasks for future samples, for example, prepare a cuvette or aspirate reagent, while processing the current sample. While the rigid predictability of FIFO queues enables the parallelization of some processing tasks, it also can prevent the modules from using opportunistic scheduling that may increase throughput by reordering tests on samples to optimize resources. For example, the internal resource conflicts of most immunoassay analyzers can be so complex that the analyzers need to interleave the tests from multiple samples in order to reach maximum efficiency. A FIFO queue can reduce the throughput of these analyzers by as much as 20%. Another challenge with FIFO queues is their inability to handle priority samples (e.g., a STAT sample). If a STAT sample needs to be processed immediately, the entire FIFO queue has to be flushed back onto the main track, delaying all other samples on the track and forcing the original module to slowly rebuild its queue.

Another type of queue is a random access (RA) queue. A carousel is an example of a physical RA queue found in analyzer modules. By aliquoting a portion of a sample into one or more vessels in a carousel ring, an analyzer module can select any of a number of samples to process at any time within the analyzer. However, carousels have many drawbacks, including added complexity, size, and cost. A carousel also increases the steady-state processing time, because a sample must be transferred into and out of the random-access queue. Processing delays depend on the implementation, such as the number of positions in a carousel. On the other hand, by having random access to samples, a local scheduling mechanism within a module can process samples in parallel, performing sub-steps in any order it desires.

In some embodiments, carousels or other RA queues can be eliminated from the modules and the sub-paths (e.g., 210) from the automation system can be used as part of an RA or FIFO queue. That is, if the travel time for a sample between any two points can be bounded to a known time that is similar to that of a carousel (such as predictably less than a portion of an operation cycle) the track 200 can be part of the queue for a given module. For example, rather than using a carousel, module 205 can utilize samples in carriers on sub-path 210. Preprocessing steps, such as reagent preparation, can be conducted prior to the arrival of a sample under test. Once that sample under test arrives, one or more portions of the sample can be aspirated into cuvettes or other reaction vessels for an assay. In some embodiments, these reaction vessels can be contained within module 205, off track, while in other embodiments, these reaction vessels can be placed in carriers on sub-path 210 to allow easy motion. If the sample under test is required to be at a module for longer than an operation cycle, or if multiple samples will be processed by the module during an operation cycle, the sub-path 210 can act as a queue for the module.

Furthermore, samples not yet under test, which may be currently located at other modules, can be scheduled for the next operation cycle. These next-cycle samples can be considered as residing in a virtual queue for module 205. A module can schedule samples to arrive during a given operation cycle for any sample on track 200. A central controller, or controllers associated with modules themselves, can resolve any conflicts over a sample for a given cycle. By giving a module a prior knowledge of the arrival time of a sample, each module can prepare resources and interleave tests or portions of tests to more efficiently allot internal resources. In this manner, modules can operate on samples in a just-in-time manner, rather than by using large physical buffers. The effect is that the virtual queue for a given module can be much larger than the physical capacity of the sub-path serving that module, and existing scheduling algorithms can be used. Effectively, each module can treat track 200 as it would treat a sample carousel in a prior art module.

It should be appreciated that by employing virtual queues, in some embodiments, multiple modules can have multiple queues and can share a single queue or samples within a queue. For example, if two modules are equipped to perform a certain assay, a sample needing that assay can be assigned to a virtual queue for that assay, which is shared between the two modules capable of handling the assay. This allows load balancing between modules and can facilitate parallelism. In embodiments where reaction vessels are placed in carriers on track 200, an assay can be started at one module (e.g., reagents prepared and/or sample mixed in) and the assay can be completed at another (e.g., a reaction is observed at another module). Multiple modules can effectively be thought of as a multi-core processor for handling samples in some embodiments. In these embodiments, scheduling algorithms for the multiple modules should be coordinated to avoid conflicts for samples during a given operation cycle.

By employing virtual queues, modules can operate on samples while the samples are in the virtual queues of other modules. This allows low latency of samples, as each sample that is placed onto track 200 can be processed as quickly as the modules can complete the tests, without having to wait through a physical queue. This can greatly reduce the number of sample carriers on track 200 at any given time, allowing reliable throughput. By allowing modules to share queues or samples, load balancing can also be used to maximize throughput of the system.

Another advantage of using virtual queues is that STAT samples can be dynamically assigned priority. For example, a STAT sample can be moved to the head of any queue for the next operation cycle in software, rather than having to use a physical bypass to leapfrog a STAT sample to the head of a largely static physical queue. For example, if a module is expecting three samples to be delivered by track 200 for assays during the next operation cycle, a scheduler responsible for assigning samples to the module can simply replace one or more of the samples with the STAT sample, and have the track 200 deliver the STAT sample for processing during the next operation cycle.

If decision points such as 214 and 216 can be streamlined such that there is no need for a queue at each decision point, the only physical queues can be within sub-paths 210, 210A, and 210B. As described above, these can be treated as RA queues or FIFO queues. If a STAT sample is placed onto track 200, RA queues within sub-paths 210, 210A, and 210B need not be flushed, as the STAT sample can be processed immediately. Any FIFO queues can be individually flushed. For example, if a STAT sample is placed onto track 200 at section 222, the sample may be routed to the appropriate analyzer 205B via the outside track and decision point 216. If there are other samples (and, by extension, the sample carriers transporting those samples) waiting in the queue in path 210B, only those samples in the queue may need to be flushed to allow a STAT sample to take priority. If the outer track 200 is presumed to take less than an operation cycle to traverse, any samples that were flushed from the queue in 210B can simply be circulated around the track and placed immediately back into the queue in path 210B immediately behind the STAT sample, eliminating any down time caused by the STAT sample.

Entry paths 220 and 222 can be used to input samples to the track 200. For example, regular priority samples can be placed onto track 200 at input 220 and STAT priority samples can be placed on input 222. These inputs can be used as outputs for samples when complete, or other ports (not shown) can be used as the output paths for used samples. Input 220 can be implemented as an input buffer, acting as a FIFO queue for input samples seeking access to the track 200. Once a sample reaches the head of the queue at input 220, it can be moved onto the track (either by being placed in a carrier or by being placed in a carrier, when it is placed in input 220). A STAT sample can enter the track 200 immediately after being placed at input 222 or, if track 200 is overcrowded, the STAT sample can enter the track at the next available uncrowded operation cycle. Some embodiments monitor the number of carriers on the track during an operation cycle and limit the total number to a manageable amount, leaving the remainder in input queues. By restricting samples at the input, track 200 can be free of traffic, allowing it to always be operated in the most efficient manner possible. In these embodiments, the transit time of a sample between two modules can be a bounded value (e.g., less than some portion of an operation cycle), allowing simplified scheduling.

In some embodiments, the track system 200 can be designed to be bidirectional. This means that sample carriers can traverse the outside path and/or any sub-paths in either direction. In some embodiments, additional sub-paths, such as 211B accessed via additional decision points 215 and 217, can assist in providing bidirectional access. Bidirectional paths can have inherent advantages. For example, if normal priority samples are always handled in the same direction, a STAT sample can be handled in the opposite direction along the sub-path. This means that a STAT sample can essentially enter the exit of the sub-path and be immediately placed at the head of the queue without requiring the queue to be flushed. For example, if a STAT sample is placed on track 200 at segment 204, it can enter path 210B via decision point 214 and proceed into path 210B to be immediately placed at the head of any queue. Meanwhile, in all of these examples, because queues are presumed to be limited generally to sub-paths, there is no need to flush queues in other modules if a STAT sample does not need immediate access to those modules. Any additional modules that need to service a STAT sample on a subsequent cycle can flush their queues at that point, providing just-in-time access to a STAT sample without otherwise disrupting the operation of each analyzer module.

Modular design also allows certain other advantages. If the automation systems within an analyzer module are adapted to take advantage of the track system contained in the module, new features can be added that use the common track. For example, a module could have its own internal reagent carousel that includes all of the reagents necessary for performing the assays prescribed for the samples. When reagents stocked in the analyzer module run low, an operator can replenish the reagents in some embodiments by simply loading additional reagents onto carriers on the track 200. When the reagents on track 200 reach the appropriate module, the module can utilize mechanical systems such as an arm or a feeder system that takes the reagents off of the track and places the reagents in the reagents store for the module.

In some embodiments, the individual track portions shown in FIG. 3, and FIG. 2A and FIG. 2B can be operated independently from one another, or can be passive. Independent carrier movement provides advantages over friction-based track systems, such as non-localized conveyor belts where the entire friction track must be moved to effect movement of a sample carrier. This means that other samples also on that track must move at the same rate. This also means that if certain sections operate at different speeds, collisions between passive carriers carrying samples can occur.

FIG. 4A depicts an exemplary carrier 250 for use with embodiments of the present invention. Carrier 250 can hold different payloads in different embodiments. One payload can be a sample tube 255, which contains a fluid sample 256, such as blood or urine. Other payloads may include racks of tubes or reagent cartridges or any other suitable cartridge. Sample carrier 250 includes a main body 260, which can house the internal electronic components describe herein. The main body 260 supports a bracket 262, which can accept a payload. In some embodiments, this is a shallow hole that is designed to accept a fluid container 255 such as a sample tube, and hold it with a friction fit. In some embodiments, the friction fit can be made using an elastic bore or a clamp that can be fixed or energized with a spring to create a holding force. In some embodiments, sample racks and reagent cartridges can be designed to also attach to the bracket 262, allowing bracket 262 to act as a universal base for multiple payload types.

Body 260 can include or be coupled to guide portion 266, which allows the carrier 250 to follow a track between decision points. Guide portion 266 can include, for example, a slot to accept one or more rails in the track, providing lateral and/or vertical support. In some embodiments, the guide portion allows the carrier 250 to be guided by walls in the track, such as the walls of a trough-shaped track. The guide portion 266 can also include drive mechanisms, such as friction wheels that allow a motor in the carrier body 260 to drive the carrier or puck 250 forward or backward on the track. The guide portion 266 can include other drive components suitable for use with the embodiments described throughout, such as magnets or induction coils.

Rewritable display 268 can be provided on the top of the carrier 250. This display can include an LCD oriented panel and can be updated in real time by the carrier 250 to display status information about sample 256. By providing the electronically rewritable display on the top of the carrier 250, the status information can be viewed at a glance by an operator. This can allow an operator to quickly determine which sample he/she is looking for when there are multiple carriers 250 in a group. By placing the rewritable display on top of the carrier 250, an operator can determine status information even when multiple carriers 250 are in a drawer or rack.

In addition to sample carriers, such as carrier 250 in FIG. 4A, carriers can include hardware that provides tools for performing maintenance functions. Exemplary maintenance carriers are shown in FIGS. 10-18 and are described below.

Figure 4B:
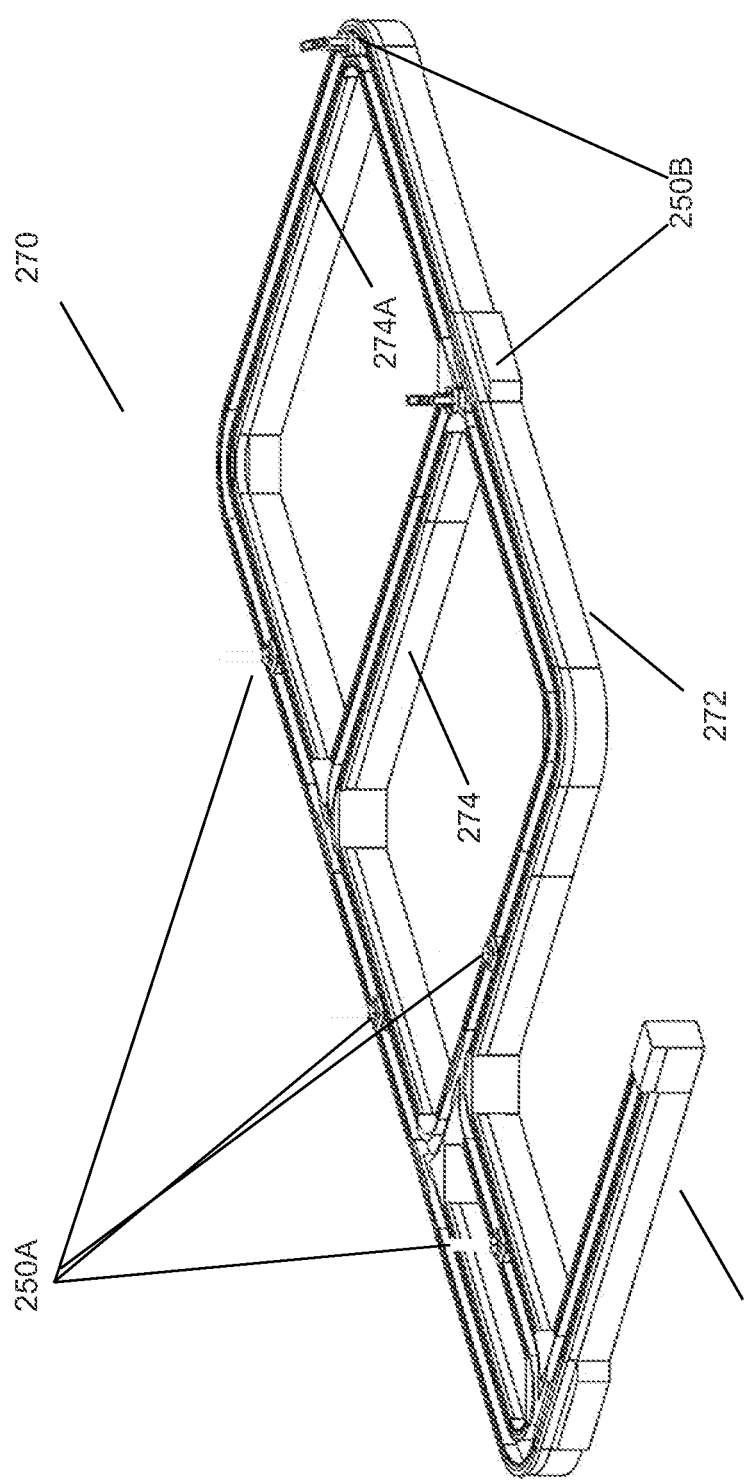
FIG. 4B is a perspective view of an exemplary track configuration that can be used with the embodiments disclosed herein.

FIG. 4B shows an exemplary track configuration 270 for use by carriers 250. In this example, carriers 250A transport sample tubes, while carriers 250B transport racks of tubes along main track 272 and/or subpaths 274 and 274A. Path 276 can be used by an operator to place samples into carriers or remove samples from these carriers.

Figure 4C:
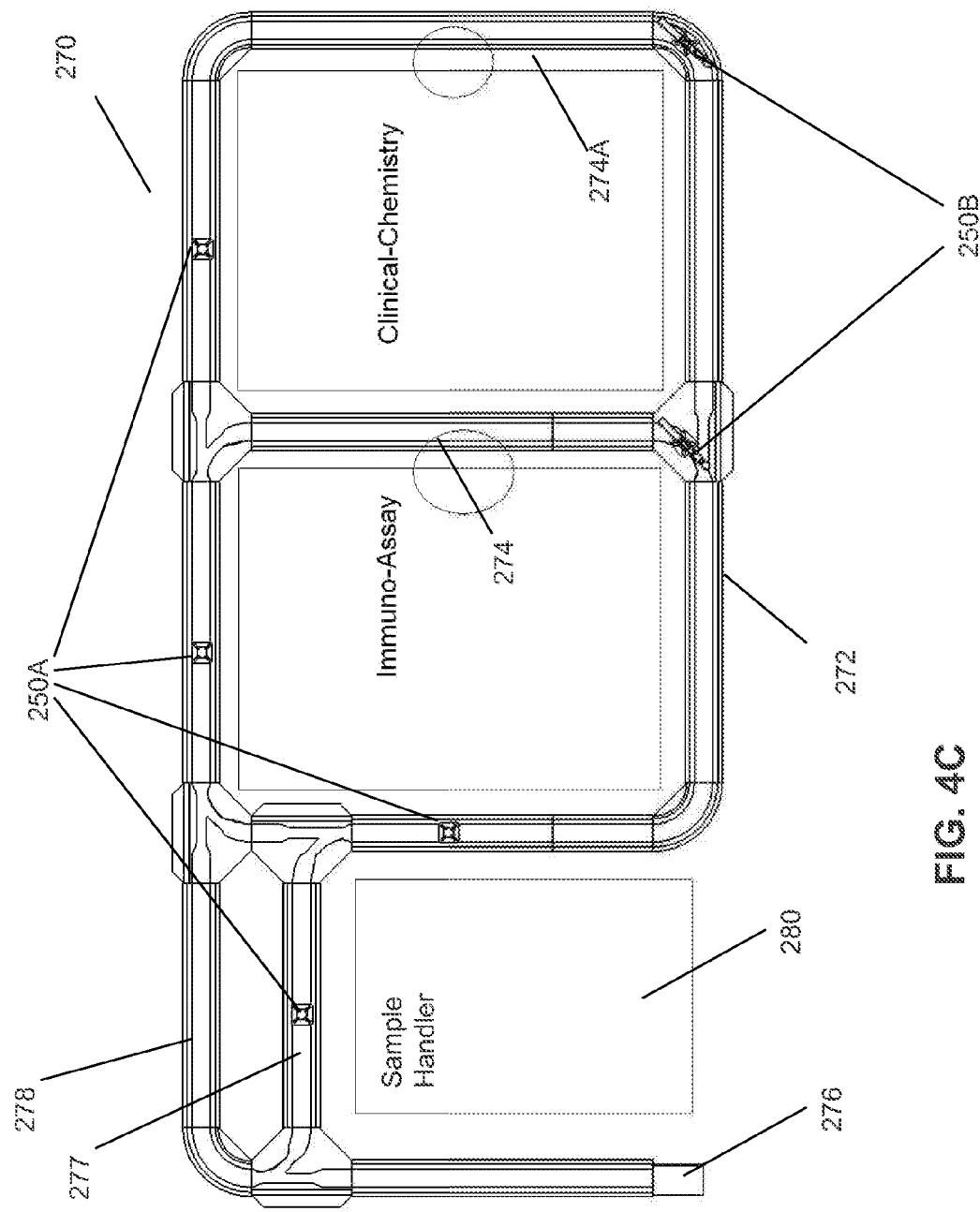
FIG. 4C is a top view of an exemplary automation systems that can be used with the embodiments disclosed herein.

FIG. 4C shows an additional view of an exemplary track configuration 270. In this example, sub-path 274 serves an immunoassay station, while sub-path 274A serves a clinical chemistry station. Input/output lane 276 can be served by a sample handler station 280 that uses sub-paths 277 and 278 to buffer samples for insertion or removal of the samples from the main track 272.

In some embodiments, the sample handler 280 can also load and unload samples or other payloads to/from the carriers 250A and 250B. This allows the number of carriers to be reduced to the amount needed to support payloads that are currently being used by the stations in track system 270, rather than having a vast majority of carriers sitting idle on tracks 277 and 278 during peak demand for the analyzer. Instead, sample trays (without the carriers disclosed herein) can be placed/removed by an operator at input/output lane 276. This can reduce the overall cost of the system and the number of carriers needed can be determined by the throughput of the analyzer, rather than based on anticipating the peak demand for the analyzer in excess of throughput.

Intelligent Carriers

Whereas some embodiments may utilize passive pucks or trays (e.g., the puck is a simple plastic or rubber brick that lacks active or autonomous systems, power, onboard processing, or control) to reduce cost and complexity, in some embodiments the added complexity and cost necessary to integrate intelligence and autonomy into individual carriers (which can include smart pucks or trays in some embodiments) can provide certain benefits. Accordingly, some embodiments of the present invention can utilize intelligent carriers to enable certain improvements over passive pucks on the friction-based tracks. For example, one disadvantage of prior art track systems is that, at each decision point, the decision for directing a puck is made by the track by rotating the puck and reading a barcode optically. Rotating and optical reading is a relatively slow process. Furthermore, this process can be redundant because the system has a prior knowledge of the identification of the sample tube when the sample tube is placed into the puck by an operator. Embodiments of the present invention can include carriers that have means to identify the contents of the sample tube (and optionally communicate this information to the automation system) without requiring the carrier to be stopped, rotated, and read optically. Some embodiments of the maintenance carriers disclosed herein utilize designs that are smart carriers, capable of navigating the automation system semi-autonomously. Similarly, some embodiments the maintenance carriers disclosed herein utilize designs that are passively navigate the automation system, their trajectory being controlled by the track and drive mechanisms therein.

For example, a carrier can include an onboard optical reader to automatically read a barcode of a payload. The results of the scan can then be stored in the memory of a carrier if the carrier has onboard processing capability. Alternatively, an outside source, such as a hand barcode reader operated by an operator at the time of placing the sample into the carrier, can communicate the barcode information of the payload to the carrier via RF signal or other known means, such as a communication protocol using temporary electrical contact or optical communication. In some embodiments, the association of the carrier with the payload can be stored external to the carrier and the identity of the carrier can be conveyed by the carrier to the system by RF, optical, or near field communication, allowing the system to assist in routing or tracking the carrier and the payload. Routing decisions can then be made by the carrier or by identifying the carrier, rather than reading a unique barcode of a payload.

By moving processing capability and/or sensor capability onto each individual carrier, the carriers can participate actively and intelligently in their own routing through the track system. For example, if individual carriers can move independently of one another either by autonomous motive capabilities or by communication with the track, certain performance advantages can be realized.

By allowing carriers to move independently, carriers can move around the track faster. One key limitation on the motion of a carrier is that it should not spill an open-tube sample. The limiting factor is generally not the velocity of the carrier in a straight line, but the acceleration and jerk experienced by the carrier (while speeding up, slowing down, or turning), which may cause splashing. For prior-art friction-based track systems, the velocity of the track is typically limited to prevent acceleration and jerk experienced by pucks from exceeding threshold amounts because the entire track moves. However, by using a track system with independently operating sections that can respond to individual carriers, or individual carriers that have independent motive capability, the acceleration of any given carrier can be tailored to limit acceleration/deceleration and jerk, while allowing the average velocity to be greater than that of traditional tracks. By not limiting the top speed of a carrier, the carrier can continue to accelerate on each track section as appropriate, resulting in a substantially higher average speed around the track. This can assist the carrier in traversing the entire track system in less than one machine cycle of the analyzer. These machine cycles can be, for instance 20 or 40 seconds.

Similarly, an autonomous carrier can know its own identity and that of its payload. This allows the carrier to actively participate or assist in the routing decision process at individual decision points. For example, upon reaching a decision point (e.g., switch, intersection, junction, fork, etc.), a carrier can communicate its identity and/or the identity of its payload to the track or any switching mechanism (or its intended route that the carrier has determined based on the payload identity), via RF or near-field communication. In this scenario, the carrier does not need to be stopped at a decision point for a barcode scan. Instead, the carrier can proceed, possibly without even slowing down, and the carrier can be routed in real time. Furthermore, if the carrier knows its destination or communicates its identity to the track (such that the track knows where the carrier is going) before the carrier physically reaches a decision point, the carrier can be made to decelerate prior to a decision point if the carrier will be turning. On the other hand, if the carrier does not need to turn at the decision point, the carrier can continue at a higher velocity because the sample carried by the carrier will not undergo cornering forces if the carrier is not turning at the decision point or a curved section of the track.

An autonomous carrier can also include onboard processing and sensor capabilities. This can allow a carrier to determine where it is on the track and where it needs to go, rather than being directed by the track (although in some embodiments, a central controller sends routing instructions to the carrier to be carried out). For example, position encoding or markers in the track can be read by a carrier to determine the carrier's location. Absolute position information can be encoded on a track surface to provide reference points to a carrier as it traverses the track. This position encoding can take many forms. The track may be encoded with optical markers that indicate the current section of the track (e.g., like virtual highway signs), or may further include optical encoding of the specific absolute location within that section of track (e.g., like virtual mile markers). Position information can also be encoded with markings between absolute position marks. These can provide synchronization information to assist a carrier in reckoning its current trajectory. The optical encoding scheme may take on any appropriate form known to one skilled in the art. These marks used by the encoding scheme may include binary position encoding, like that found in a rotary encoder, optical landmarks, such as LEDs placed in the track at certain positions, barcodes, QR codes, data matrices, reflective landmarks, or the like. General position information can also be conveyed to the carrier via RF/wireless means. For example, RFID markers in the track can provide near field communication to the carrier to alert the carrier that it has entered a given part of the track. In some embodiments, local transmitters around or near the track can provide GPS-like positioning information to enable the carrier to determine its location. Alternatively, sensors in the track, such as Hall effect sensors or cameras, can determine the position of individual carriers and relay this information to the carrier.

Similarly, the carrier can have sensors that indicate relative motion, which provide data that can be accumulated to determine a position between absolute position marks. For example, the carrier may have gyroscopes, accelerometers, or optical sensors that observe speckle patterns as the carrier moves to determine velocity or acceleration, which can be used to extrapolate a relative position. In some embodiments, components include a light source and an image sensor that can be used to observe the relative motion of the track surface with respect to the carrier to determine a real-time trajectory estimate. For example, after reckoning its position with an absolute position mark, the carrier can observe successive images of a track surface and compare these images to determine the direction and magnitude of motion. This can be used to determine real-time position, velocity, acceleration, and jerk, or estimates thereof. In addition, synchronous marks, such as marks placed at regular intervals in the track, can be used to reckon the carrier's position between absolute position marks and can correct errors that may have accumulated in the real-time trajectory information determined from observation of the relative motion of the surface of the track. This can allow a lower sampling frequency or less precise components in the position decoding imaging sensor.

Because a carrier can know where it is and its motion relative to the track, a carrier can essentially drive itself, provided it knows its destination. The routing of the carrier can be provided in many different ways in various embodiments. In some embodiments, when a carrier is loaded with the sample, the system can tell the carrier the destination analyzer station. This information can be as simple as the identification of the destination station in embodiments where the carrier has autonomous routing capability. This information can also be detailed information such as a routing list that identifies the specific path of the individual track sections and decision points that a carrier will traverse. Routing information can be conveyed to the carrier via any communication method described herein, such as RF communication, near-field/inductive communication, electrical contact communication, or optical communication.

In an exemplary embodiment, when an operator scans the barcode of the sample tube and places it in a carrier, the system determines the identity of the carrier and matches it with the identity of the sample. The system then locates the record for the sample to determine which tests the sample must undergo in the analyzer. A scheduler then allocates testing resources to the sample, including choosing which tests will be done by individual testing stations and when the sample should arrive at each testing station for analysis. The system can then communicate this schedule (or part of the schedule) to the carrier to inform the carrier of where it needs to go, and optionally when it needs to go and/or when it needs to arrive.

Once the carrier is placed onto the track system, the routing capabilities and location acquisition systems of the carrier enable the carrier to determine where it is on the track and where it needs to go on the track. As the carrier traverses the track, the carrier reaches individual decision points and can be directed along the main track or along sub-paths as appropriate. Because each carrier operates independently from one another, a carrier can do this quite quickly without necessarily stopping at each decision point and without waiting for other carriers in a queue. Because these carriers move quickly, there is less traffic on the main sections of the track, which reduces the risk of collision or traffic jams at decision points or corners in the track (e.g., sections where carriers might slow down to avoid excessive forces on the sample).

Motive force can be provided to the carriers in many ways. In some embodiments, the track actively participates in providing individualized motive force to each carrier. In some embodiments, motive force is provided by electromagnetic coils in the track that propel one or more magnets in the carrier. An exemplary system for providing this motive force is the track system provided by MagneMotion, Inc., which can generally be understood by the description of the linear synchronous motors (LSMs) found in US Published Patent Application 2010/0236445, assigned to MagneMotion, Inc. These traditional systems utilizing this magnetic motion system have included passive carriers that lack the integrated intelligence of the carriers described herein, and all routing and decisions are made by a central controller with no need for active carriers that participate in the routing and identification process.

In embodiments that utilize magnetic motion, the electromagnetic coils and the magnets operate as an LSM to propel each individual carrier in the direction chosen with precise control of velocity, acceleration, and jerk. Where each coil on the track (or a local set of coils) can be operated independently, this allows highly localized motive force to individual carriers such that individual carriers can move with their own individually tailored accelerations and velocities. Coils local to a carrier at any given moment can be activated to provide precise control of the direction, velocity, acceleration, and jerk of an individual carrier that passes in the vicinity of the coils.

In some embodiments, a track may be comprised of many individually articulable rollers that act as a locally customizable friction track. Because individual micro-sections of the track can be managed independently, rollers immediately around a carrier may be controlled to provide individualized velocity, acceleration, and jerk. In some embodiments, other active track configurations can be used that provide localized individual motive force to each carrier.

In some embodiments, the track may be largely passive, providing a floor, walls, rails, or any other appropriate limitations on the motion of a carrier to guide the carrier along a single dimension. In these embodiments, the motive force is provided by the carrier itself. In some embodiments, each individual carrier has one or more onboard motors that drive wheels to provide self-propelled friction-based motive force between the track and the carrier. Unlike traditional friction tracks, where the track is a conveyor, carriers with driven wheels can traverse the track independently and accelerate/decelerate individually. This allows each carrier to control its velocity, acceleration, and jerk at any given moment to control the forces exerted on its payload, as well as traverse the track along individually tailored routes. In some embodiments, permanent magnets may be provided in the track and electromagnets in the carrier may be operated to propel the carrier forward, thereby acting as an LSM with the carrier providing the driving magnetic force. Other passive track configurations are also contemplated, such as a fluid track that allows carriers to float and move autonomously via water jets or the like, a low friction track that allows carriers to float on pockets of air provided by the track, (e.g., acting like a localized air hockey table), or any other configuration that allows individual carriers to experience individualized motive forces as they traverse the track.

Figure 5:
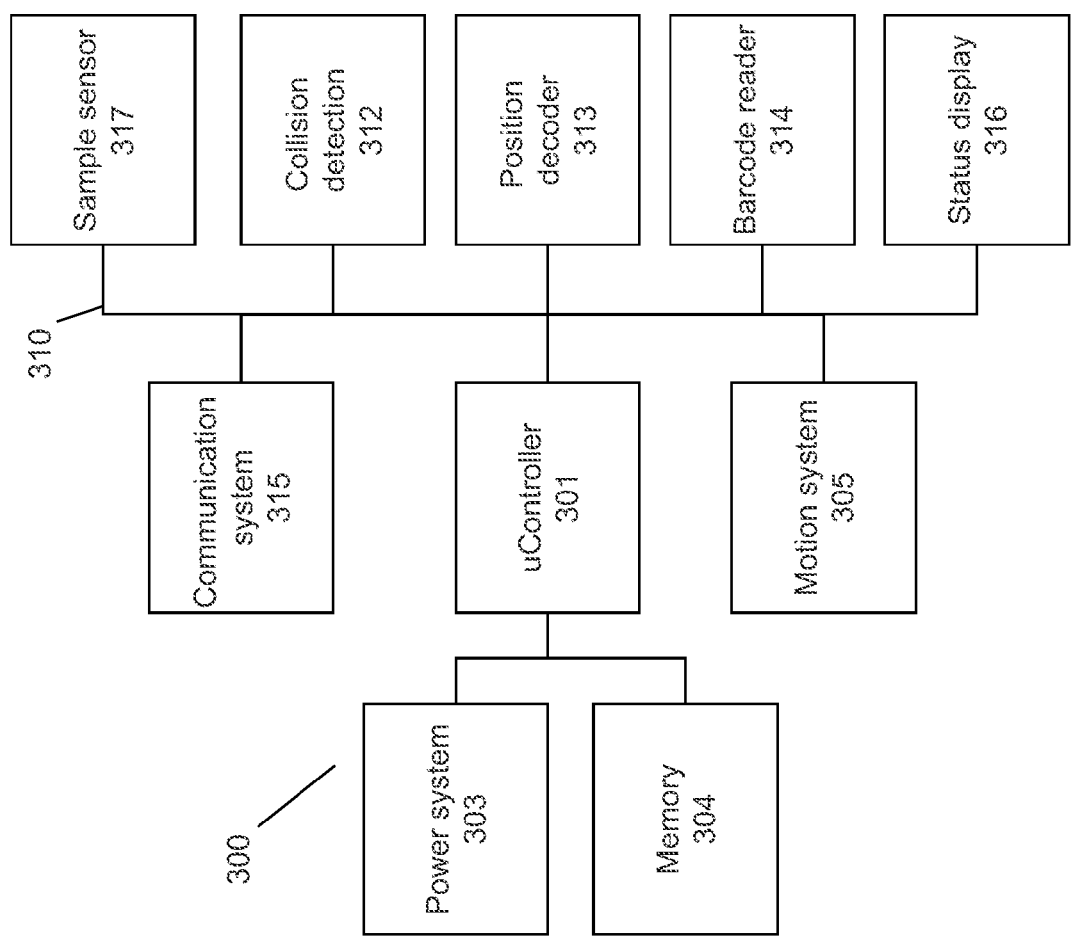
FIG. 5 is a system block diagram of the control systems, including onboard active carriers, that can be used with certain embodiments disclosed herein.

FIG. 5 shows a top level system diagram of the control systems and sensors for an exemplary intelligent autonomous carrier 300. Carrier 300 is controlled by a microcontroller 301 that includes sufficient processing power to handle navigation, maintenance, motion, and sensor activities needed to operate the carrier. Because the carrier is active and includes onboard electronics, unlike prior art passive carriers, the carrier includes an onboard power station. The details of this station vary in different embodiments of the present invention. In some embodiments, power system 303 comprises a battery that may be charged as the carrier operates, while, in other embodiments, the battery is replaceable or can be manually charged when the carrier is not operating. Power system 303 can include the necessary charging electronics to maintain a battery. In other embodiments, the power system 303 comprises a capacitor that may be charged by inductive or electrical contact mechanisms to obtain electrical potential from the track itself, in much the same way a subway car or model train might receive power.

Microcontroller 301 communicates with system memory 304. System memory 304 may include data and instruction memory. Instruction memory in memory 304 includes sufficient programs, applications, or instructions to operate the carrier. This may include navigation procedures as well as sensor handling applications. Data memory in memory 304 can include data about the current position, speed, acceleration, payload contents, navigational plan, identity of the carrier or payload, or other status information. By including onboard memory in carrier 300, the carrier can keep track of its current status and uses information to intelligently route around the track or convey status information to the track or other carriers.

Microcontroller 301 is responsible for operating the motion system 305, sensors 312, 313, and 314, communication system 315, status display 316 and sample sensor 317. These peripherals can be operated by the microcontroller 301 via a bus 310. Bus 310 can be any standard bus, such as a CAN bus, that is capable of communicating with the plurality of peripherals, or can include individual signal paths to individual peripherals. Peripherals can utilize their own power sources or the common power system 303.

Motion system 305 can include the control logic necessary for operating any of the motion systems described herein. For example, motion system 305 can include motor controllers in embodiments that use driven wheels. In other embodiments, motion system 305 can include the necessary logic to communicate with any active track systems necessary to provide a motive force to the carrier 300. In these embodiments, motion system 305 may be a software component executed by microcontroller 301 and utilizing communication system 315 to communicate with the track. Devices such as motors, actuators, electromagnets, and the like, that are controlled by motion system 305 can be powered by power system 303 in embodiments where these devices are onboard the carrier. External power sources can also provide power in some embodiments, such as embodiments where an LSM provides motive force by energizing coils in the track. In some embodiments, motion system 305 controls devices on or off the carrier to provide motive force. In some embodiments, the motion system 305 works with other controllers, such as controllers in the track, to coordinate motive forces, such as by requesting nearby coils in the track be energized or requesting the movement of local rollers. In these embodiments, motion system 305 can work together with communication system 315 to move the carrier.

Carrier 300 can include one or more sensors. In some embodiments, carrier 300 includes a collision detection system 312. Collision detection system 312 can include sensors at the front or back of a carrier for determining if it is getting close to another carrier. Exemplary collision detection sensors can include IR range-finding, magnetic sensors, microwave sensors, or optical detectors. Whereas many prior art pucks are round, carrier 300 may be directional, having a front portion and a rear portion. By having a directional geometry, carrier 300 can include a front collision detector and a rear collision detector.

In some embodiments, collision detection information can include information received via the communication system 315. For example, in some embodiments, the central controller for the track can observe the location and speed of carriers on the track and evaluate collision conditions and send updated directions to a carrier to prevent a collision. In some embodiments, nearby carriers can communicate their positions in a peer-to-peer manner. This allows carriers to individually assess the risk of collision based on real-time position information received from other carriers. It will be understood that in embodiments where the carrier receives trajectory information about other carriers, or decisions are made with the help of a centralized controller that has access to trajectory information of nearby carriers, the carriers need not be directional, and can include sensors or receivers that do not depend on a given orientation of a carrier.

Carrier 300 can also include a position decoder 313. This sensor can extrapolate the carrier's position as described herein. For example, position decoder 313 can include a camera or other optical means to identify landmarks in the track, or observe optical encoding in the track. In some embodiments, position decoder 313 can also include inertial sensors, magnetic sensors, or other sensors sufficient to determine a carrier's current position, direction, velocity, acceleration, and/or jerk.

Carrier 300 can optionally include a barcode reader 314. If equipped with the barcode reader 314, carrier 300 can observe the barcode of its payload at the time the samples are loaded onto the carrier or at any time thereafter. This prevents the need for a carrier to stop at individual decision points to have the system read the barcode of a sample tube. By reading and storing the identity of the sample tube, or conveying this information to the overall system, a carrier may more efficiently traverse the track system because routing decisions can be made in advance of reaching a decision point. Alternatively, where a system knows the identity of the sample when it is placed onto the carrier, the system can include an external barcode reader and can convey the identity of the payload to the carrier for storage and memory 304 via communication system 315.

Communication system 315 can comprise any mechanisms sufficient to allow the carrier to communicate with the overall automation system. For example, this can include an XBee communication system for wireless communication using an off-the-shelf communication protocol, such as 802.15.4, any appropriate version of 802.11, or any standard or proprietary wireless protocol. Communication system 315 can include a transceiver and antenna and logic for operating an RF communication protocol. In some embodiments, communication system 315 can also include near-field communication, optical communication, or electrical contact components. Information conveyed via the communications system to/from carrier 300 is described throughout this application.

In some embodiments, the carrier can also include a status display module 316. The status display module 316 can include a controller and rewritable electronic display, such as an LCD panel or E-ink display. In some embodiments, the controller is treated as an addressable portion of memory, such that the microcontroller 301 can easily update the status display 316.

In some embodiments, the carrier also includes sample sensor 317. This sensor can be used to indicate the presence or absence of a sample tube in the carrier's tube bracket. In some embodiments, this is a momentary mechanical switch that is depressed by the presence of a tube and not depressed when a tube is absent. This information can be used to determine the status of a tube, which can assist in the display of status information by status display module 316.

Routing

The desire for rapid transit times within an analyzer system can make routing difficult. In prior art systems, rapid routing is less critical because samples are generally stopped, singulated, and scanned at each decision point. In those systems, the routing decision for a given decision point can be made while the sample is stopped. In some embodiments, substantially instantaneous trajectory observation and control is conducted onboard each carrier to facilitate real-time control, while the overall routing decisions are made by a central controller that manages a group of carriers. Therefore, in some embodiments of the present invention, the carriers act like semi-autonomous robots that receive global routing instructions from a central controller, but make local motion decisions substantially autonomously. In other embodiments, carriers may move responsive to a track controlled by the central controller, such as a friction track or a track having a linear synchronous motor capable of moving carriers individually with magnetic forces.

For example, when a carrier receives a sample (e.g., a patient fluid sample or other payload) a central controller managing one or more carriers determines the schedule for that carrier and instructs the carrier where to go on the track of, for example, an in-vitro diagnostics automation system. This instruction can be a next-hop instruction (e.g., identifying the next leg of a route), such as going to a given decision point, moving forward to the next decision point, or turning at a given decision point. In some embodiments, the instructions can include a complete or partial list of track segments and decision points to be traversed and whether to turn at each decision point. These instructions can be communicated to the carrier from a central controller via any conventional means, including wireless or contact electrical signaling, as explained throughout this disclosure.

While following the instructions, each carrier can make a determination of the appropriate velocity, acceleration, and jerk (as used herein, acceleration includes deceleration). This can include a real-time decision of whether the carrier must slow down to avoid collision or to enter a curve without causing excessive lateral forces, or slow down before the next decision point. These decisions can be made with the assistance of any onboard sensors, as well as external information received by the carrier, such as information about the position and trajectory of nearby carriers. For example, accelerometers and/or track encoding information can be used to determine the current velocity, acceleration, and jerk, as well as the current position of a carrier. This information can be used by each carrier to determine its trajectory and/or can be conveyed to other carriers. Collision detectors, such as RF rangefinders, can determine whether or not a potential collision condition exists to assist the carrier in determining whether it needs to slow down and/or stop. This collision determination can include trajectory information about the current carrier, as well as the trajectory information about surrounding carriers received by the current carrier through observation or by receiving information from a central scheduler for the track.

Figure 6:
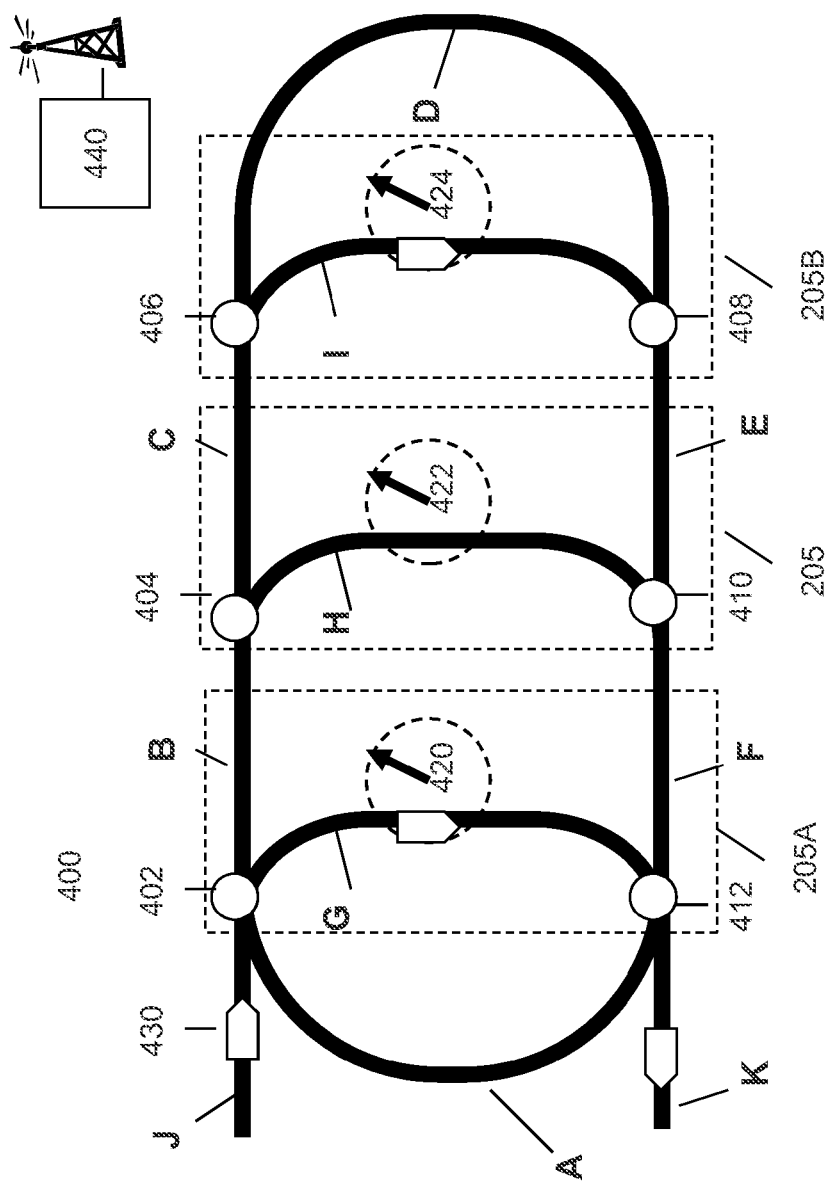
FIG. 6 is a diagrammatic view of exemplary routes in an exemplary track configuration that can be used for navigation of sample carriers in certain embodiments.

FIG. 6 shows an exemplary routing scenario in automation system 400. Carrier 430 receives routing instructions from central management processor 440 via RF signaling. Central management processor 440 can participate in monitoring and directing carriers, including issuing routing instructions and scheduling the movement and dispatch of carriers. Central management processor 440 can be part of the central controller and/or local controllers that interact with individual modules or stations. Central or local controllers can also act at the direction of central management processor 440. Central management processor 440 can include one or more processors operating together, independently, and/or in communication with one another. Central management processor 440 can be a microprocessor, software operating on one or more processors, or other conventional computer means suitable for calculating the schedule for multiple carriers within the track system 400.

Central management processor 440 can receive position information from multiple carriers, as well as any sensor information from sensors in the track system 400 and/or information reported by the carriers. Carrier 430 can be any suitable embodiment of a carrier, such as carrier 300, shown in FIG. 5. Central management processor 440 uses the status information of the carriers and track as well as the identity of samples or other payload carried by the carriers and the required assays to be performed by the system on these samples.

The exemplary track 400 shown in FIG. 6 includes a first curve segment A, that connects to straight segment B and a pullout segment G, (e.g., a segment that serves a testing station), which serves analyzer/testing station 205A and pipette 420, via decision point 402. Segment B connects to straight segment C and a pullout segment H, which serves analyzer/testing station 205 and pipette 422, via decision point 404. Segment C connects to curved segment D, which serves sample handling station 205C and pullout segment I, which serves analyzer/testing station 205B and pipette 424, via decision point 406. Segment D connects to straight segment E and the other end of pullout segment I, via decision point 408. That is, there are different paths between decision points 406 and 408—segments D and I, (where segment I is a pullout that can be used to deliver samples to interact with pipette 424). Segment E connects to straight segment F and the other end of pullout segment H, via decision point 410. Segment F connects to curved segment A and the other end of pullout segment G, via decision point 412. In some embodiments, track 400 includes input and output lanes J and K, which can be used to add or remove carriers at decision points 402 and 412.

In some embodiments, decision points 402-412 are passive forks in the track that carrier 430 can navigate to select a proper destination segment. In other embodiments, decision points 402-412 are active forks that can be controlled by carrier 430 or central management processor 440. In some embodiments, decision points 402-412 are electromagnetically controlled switches that respond to requests by carrier 430, such as via RF or near-field communication. In some embodiments these electromagnetically controlled switches have a default position, such as straight, that the switch will return to once a carrier has been routed. By using default positions for decision points, a carrier may not need to request a position at each decision point, unless it needs to be switched at that decision point.

Scheduler central management processor 440 assigns carrier 430 a first route, Route 1, to place the carrier 430 and its payload within reach of pipette 420. Carrier 430 is instructed to travel along segment J to decision point 402 and travel onto segment G to stop at a position accessible to pipette 420. In some embodiments, carrier 430 receives the instructions and determines its current location and trajectory to determine a direction and trajectory to use to reach decision point 402. Carrier 430 can also take into account that it will be making a hard right turn at decision point 402 onto segment G. In some embodiments, decision point 402 includes a switching mechanism in the track that can operate under the control of carrier 430. In these embodiments, carrier 430 communicates with the track on approach to decision point 402 to request switching onto segment G. In other embodiments, carrier 430 may have a steering mechanism (such as moveable guide wheel, directional magnets, asymmetric brakes, or the like) that allows carrier 430 to make a right turn onto segment G at decision point 402, without the assistance of an external gate integrated into the track. In these embodiments, carrier 430 engages the steering mechanism at decision point 402 to make the turn onto segment G.

This determination can be based on observing the position encoding in the track, including consulting the onboard memory of the last known position. Near-field communication from the track can also be used to provide an identification of the current track and encoding scheme being used by the track. Carrier 430 can take into account that it will be making a hard right turn at decision point 402 onto segment G. Using position encoding, carrier 430 can determine where it is in relation to decision point 402 on track J and adjust this trajectory accordingly, to ensure that it approaches the decision point with appropriate velocity.

Carrier 430 can determine its rough location—its current track section, such as section J, by reading encoding in the track, such as optical encoding, or RFID tags. In some embodiments, carrier 430 uses multiple means to determine its location within the track system 400. For example, RFID tags can be used to determine generally on which track segment the carrier 430 is located, while optical encoding or other precise encoding can be used to determine the position within that track segment. This encoding can also be used to determine velocity, acceleration, or jerk by observing changes in the encoding (e.g., derivatives from the position information).

Carrier 430 can use the identification of the current track section to determine the appropriate route to the destination section either by explicit instruction received by the central management processor 440 or by looking up an appropriate route in an onboard database in memory 304, as shown in the onboard control systems in FIG. 5. In some embodiments, the carrier 430 has an understanding of how to reach section G from section J based on a map stored in the memory of carrier 430 in memory 304. This map can include a simple lookup table or a tree of track sections where each node is linked by the corresponding decision points, or vice versa. For example, upon identifying that the carrier is currently in the track section J, the onboard database can inform carrier 430 to proceed to decision point 402 to be switched to the right onto section G.

As shown in FIG. 6, carrier 430 responds to instructions for Route 1 by proceeding onto section G and stopping at a position near pipette 420. Once the carrier 430 is stopped, it can receive additional instructions from the analyzer/testing station controlling pipette 420. For example, analyzer 205A can control pipette 420 and can instruct carriers on section G to position themselves at precise points along section G. This allows analyzer/testing stations to treat track sections as random access queues. For example, once carrier 430 stops on section G, additional instructions can be conveyed via central management processor 440 or directly from analyzer 205A to the carrier 430 via RF transmission or other means, such as local optical or inductive/near-field signals. These instructions can include halting while another carrier interacts with pipette 420, and subsequently proceeding to a position accessible to pipette 420, when analyzer 205A is ready to perform one or more assays on the sample carried by carrier 430.

Once analyzer/testing station 205A has finished interacting with the sample carried by carrier 430, additional routing instructions can be sent to the carrier 430 from the central management processor 440. For example, Route 2 can include routing instructions to proceed to section H to interact with pipette 422. In some embodiments, the routing tables contained within onboard memory 304 of carrier 430 have sufficient information about the track layout to allow the carrier to route itself to section H. In other embodiments, a list of routing steps can be transmitted to carrier 430 via central management processor 440. It will be appreciated that other embodiments can include conveying any subset of the route to carrier 430 and/or sending routing instructions in a piecemeal fashion, such that carrier 430 always knows the next routing step, and optionally subsequent routing steps.

In this example, carrier 430 receives a route list representing Route 2 from central management processor 440 instructing it to proceed via section G to decision point 412. At decision point 412, carrier 430 will initiate switching onto section A by interacting with a gate or by turning as described above. Carrier 430 can take into account curved track conditions on section G and section A to ensure that acceleration and jerk conditions do not exceed a threshold requirement for the sample it carries. This can prevent spillage or instability during transit. The route information received by carrier 430 then instructs carrier 430 to proceed through decision point 402 without turning. The trajectory used in Route 2 when approaching decision point 402 can be different (e.g., faster) from that used during Route 1, because carrier 430 knows that it does not need to make a sharp right turn onto section G. In some embodiments, this allows carrier 430 to approach decision point 402 with a substantially greater velocity during Route 2 than during Route 1. By traversing decision point 402 faster if carrier 430 is not turning, carrier 430 can complete Route 2 in less time than embodiments in which carrier 430 must slow down for possible switching at each decision point. This is an improvement over the prior art, where carriers are typically halted and singulated, regardless of whether the carrier is turning or not.

After passing decision point 402, carrier 430 proceeds onto section B. At decision point 404, carrier 430 proceeds to section C. At decision point 406, carrier 430 prepares and turns onto section I, where it stops for interaction with pipette 424. Like section G, section I can act as a queue for pipette 424 and carrier 430 can be controlled under local instruction by the analyzer/testing station 205B served by section I.

When pipette 424 is done interacting with carrier 430, central management processor 440 can provide new routing instructions to carrier 430 instructing carrier 430 to proceed onto an output path K. Route 3 can be handled in the same manner as Route 1 and Route 2. Upon receiving instructions for Route 3, carrier 430 proceeds down section I to decision point 408 where it turns back onto a main track section E and proceeds past decision point 410, track section F, and decision point 412 (without needing to slow down in some embodiments), and onto section K where the carrier 430 and/or the sample can be removed from the system by an operator. Carrier 430 can then be reused for samples at input section J.

Figure 7:
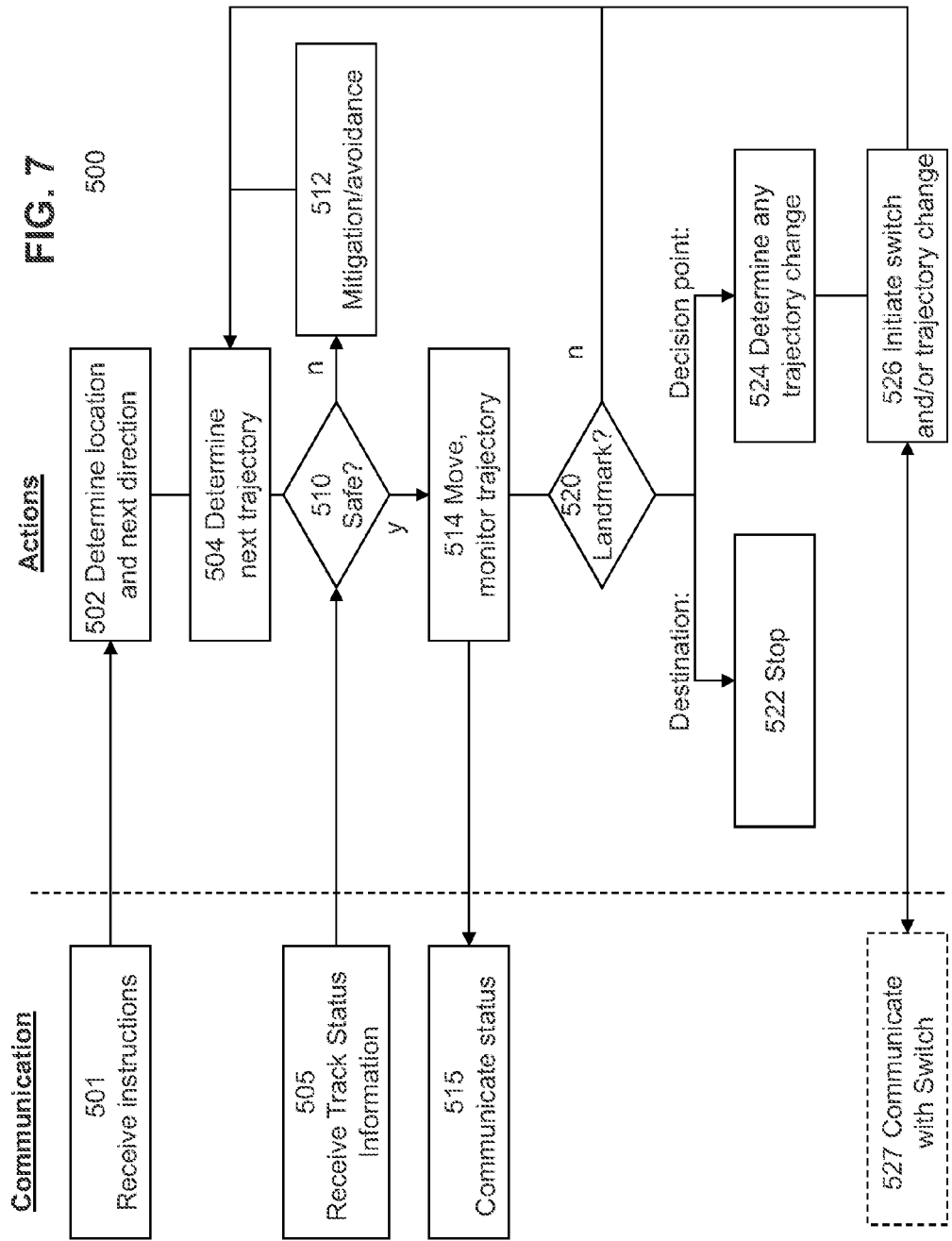
FIG. 7 is a flow diagram showing the operation of the navigation of sample carriers in certain embodiments.

FIG. 7 shows a general operational diagram of carrier 430 as it follows routing instructions. As can be seen in method 500, the actions can be taken by the carrier with minimal control by, or interaction with, a central scheduler, such as a central management controller. At step 501 the carrier receives routing instructions from, for example, a central scheduler. In this example, the routing instructions include enough information for the carrier to determine its entire route to a destination point in the track system. These instructions can include a list of all routing points, including decision points to turn at and sections to traverse. In some embodiments, routing instructions can include the destination point and onboard routing information can be used by the carrier to determine the best route to take. It will be appreciated that, when at least a main track is unidirectional, the routing calculation by the carrier is fairly simple and can comprise any known method including searching a tree of nodes and sections or searching a lookup table of possible route permutations.

These instructions can also include velocity and acceleration motion profiles for each section. In some embodiments, velocity and acceleration for each section of track can be calculated by the carrier based on its payload and based on information in an onboard database, such as length of track, curvature of track, location of decision points, the type of sample or payload being carried, and consideration of whether the carrier will turn or proceed in the same direction upon reaching a decision point. In some embodiments, the routing information received at step 501 also includes timing information to instruct the carrier when to begin transit and/or when to complete transit.

Upon receiving routing instructions and beginning transit, the carrier determines its current location and optionally the direction needed to begin its route at step 502. In a general sense, a carrier can only move in two directions, forward or backwards and, in some embodiments, initiate a turn while moving. Because of the simplified movement model, a carrier can begin its transit even if it only has a rough understanding of its current location, such as by acquiring the current track section by RFID information. In some embodiments, the carrier uses more precise encoding in the track to determine its current location within a track section before proceeding.

Once the current position and necessary direction is determined, the carrier can begin transit at step 504. By using an understanding of the location on the track, geometry of the current track, distance to the next decision point, type of sample/payload, and current velocity, the carrier can determine a safe acceleration profile to begin transit. For example, if a carrier is a large distance away from the next decision point and is currently stopped, the carrier can begin accelerating at a maximum acceleration for the sample. In some embodiments, the acceleration of the carrier is ramped up to avoid exposing the sample to a high degree jerk.

Figure 8:
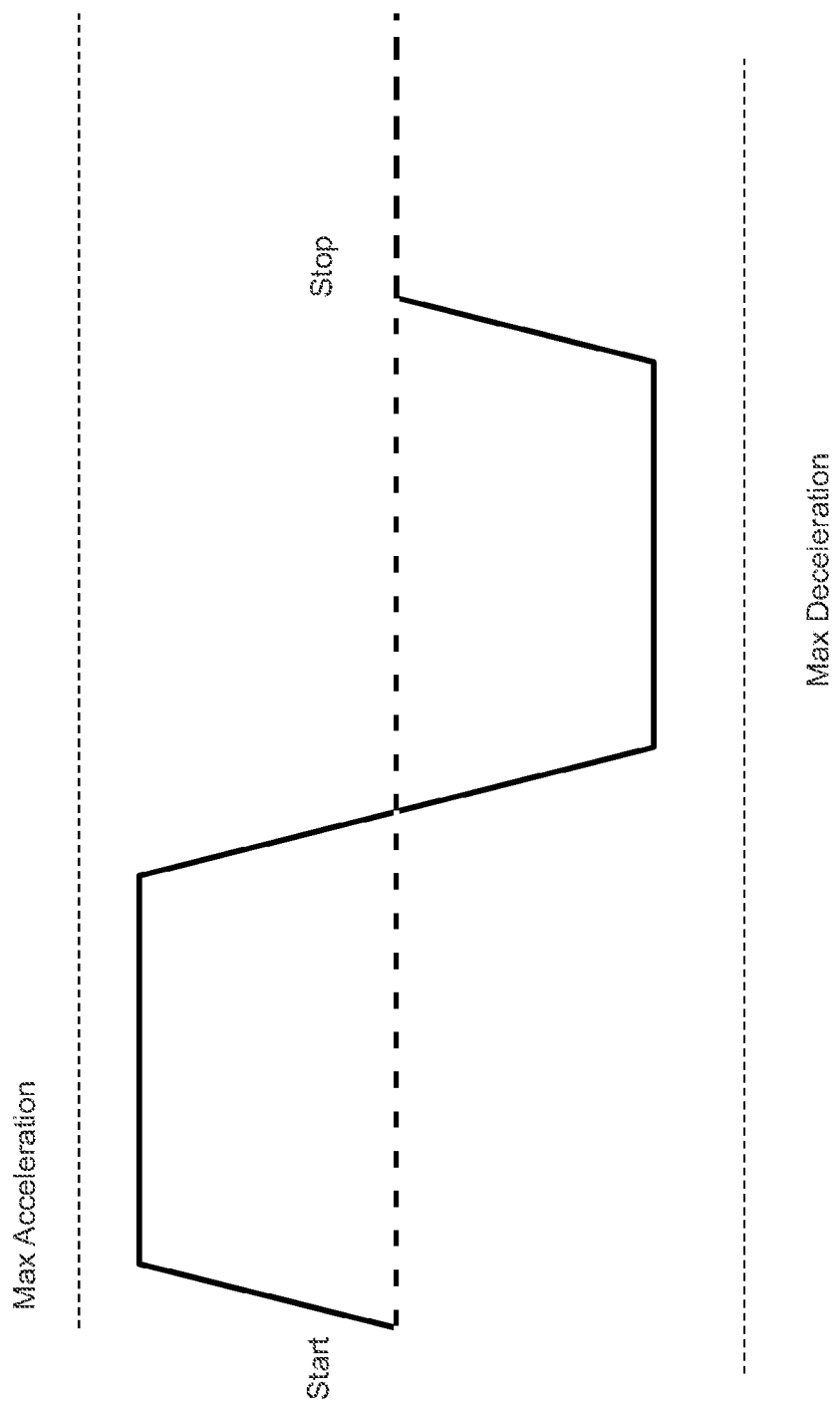
FIG. 8 is an exemplary acceleration profile used by sample carriers in certain embodiments.

FIG. 8 shows an exemplary acceleration motion profile that can be used to limit jerk and acceleration, while minimizing transit time. By using a trapezoidal acceleration profile, acceleration is ramped up to avoid unnecessary jerk until acceleration reaches a safe amount that is less than a threshold amount to avoid damaging or spilling the sample. By ensuring that acceleration is less than a threshold amount, a carrier may have some acceleration available to mitigate collisions or handle other unexpected situations without exceeding an acceleration threshold for the payload. Generally, maximum velocity will be reached midway between a start point and a stop point. In some embodiments, there is no top speed for a straight section of track, but curved sections of track are governed by a top speed to prevent excessive lateral acceleration. These speed limits and acceleration thresholds may be are known to an intelligent carrier, and may be accessible in onboard memory. The exact motion profile used by a carrier can vary depending on the payload being carried. For example, empty carriers or carriers transporting reagents or non-sample payloads may utilize a motion profile that has higher limits than a motion profile that carries a sample.

Unlike traditional friction tracks, which are governed by a fixed velocity of the track, some embodiments of the present invention can be enable dynamic acceleration profiles and allow carriers to move at much greater average velocity than the prior art. In some embodiments, it is generally desirable to limit the maximum transit time between any points within the track system to less than a portion of an operation cycle of the clinical analyzer. For example, if the maximum distance between any points on a track system is 25 m and the operation cycle time is 20 seconds, it may be desirable to ensure that the average velocity of the carrier, including all turns, acceleration, deceleration, starting, and stopping, is sufficient to traverse 30 m in 5 seconds or less, or 6 m/s (~2.1 km/hr). Because a majority of the time in transit is spent accelerating or decelerating, it will be appreciated that the maximum velocity of the carrier on a straightaway can be substantially higher than this average velocity.

Because jerk and acceleration should be limited for samples, real-time control of acceleration is desired. This goal is furthered by giving control of acceleration to the carrier itself so that it can monitor its current trajectory using accelerometers or other sensors. The carrier can dynamically change its trajectory based on track conditions such as location, traffic, and the need to slow down for an upcoming turn. In this manner, the carrier can be responsible for monitoring and controlling its own dynamic stability conditions.

Referring back to FIG. 7, at step 510, the carrier determines whether or not it is safe to continue accelerating or decelerating in accordance with the trajectory determined in step 504. Step 510 can include collision detection or checking for other unexpected obstructions or a system-wide or carrier-specific halt command. In some embodiments, the decision at step 510 is based on collision detection sensors, including RF rangefinders, but can also include status information about the track received from the central management controller or from other carriers at step 505. This status information can include, for example, position and trajectory information about surrounding carriers or updated commands such as a halt instruction or new route instructions.

If the carrier determines at step 510 that it is not safe to continue with the planned trajectory, the carrier can take steps to mitigate or avoid a collision at step 512. For example, if it is determined that the acceleration profile will place the carrier dangerously close to another carrier, the carrier can begin slowing down. In some embodiments, the decision to slow down to avoid collision is based on an extrapolation of the current trajectory and the observed trajectory of the other carrier. If it is determined that the current trajectory will cause the carrier to come within an unsafe following distance from the carrier ahead of it, the mitigation procedure will be initiated. In some embodiments, each carrier is modeled as having a collision zone into which it is unsafe to enter. This collision zone moves with the carrier. If a carrier senses that it will invade a collision zone of another carrier (or another carrier will invade the instant carrier's collision zone), the carrier can mitigate the collision by decelerating (or accelerating to avoid a rear end collision in some embodiments).

After the carrier decelerates/accelerates to mitigate a collision, the carrier proceeds back to step 504 to determine an updated trajectory that takes into account the new collision avoidance conditions. If no unsafe condition is detected, the carrier proceeds with implementing its trajectory at step 514 (e.g., proceed with a portion of the trajectory before repeating steps 504-510 to allow for continuous monitoring of conditions). This can include accelerating or decelerating and observing track encoding and accelerometer information to determine its current status and trajectory. In some embodiments, the carrier will communicate its current status, including location, trajectory, and/or planned trajectory to the central controller and/or other carriers to assist in routing and collision avoidance at step 515.

As the carrier begins iteratively implementing its planned trajectory, it observes the track for upcoming landmarks, such as its terminal destination or an upcoming decision point at step 520. These landmarks can be identified via important features in the track, such as a warning or braking LED, by extrapolating the distance to a landmark from the observed encoding, or by some combination thereof. If no landmark is upcoming, the carrier continues to step 504 and continues iteratively calculating and implementing a planned trajectory.

In this example, there are two types of important landmarks. The first landmark is the destination of the carrier. The carrier can determine if it is nearing its destination based on track encoding or a landmark feature such as an LED and uses information to begin stopping or complete a stopping procedure at step 522. For example, a carrier may be instructed to stop at a precise location accessible to a pipette. This precise location may include an LED in the wall or floor of the track to assist a carrier in the stopping at a precise location with millimeter accuracy. In some embodiments, the calculated trajectory at step 504 is used to get a carrier in a rough location of its destination, while a stopping procedure at step 522 is used to determine the precise stopped location, such as by searching for a nearby LED landmark and stopping at the appropriate position.

Another important landmark is a decision point. Encoding or warning LEDs in the track can convey the position of an upcoming decision point to a carrier. For example, a central management controller may illuminate an LED at a braking position on the track some distance before a decision point to alert the carrier to decelerate to prevent unnecessary acceleration or collision at decision point. In other embodiments, the carrier extrapolates the relative position of an upcoming decision point from the track encoding and uses this distance to update its trajectory, if necessary, at step 524. At step 524, a carrier determines the relative location of a decision point and determines, based on its routing information, if the carrier will be turning or proceeding at the decision point. If the carrier will be turning, it may be necessary to update the trajectory to begin decelerating so that the velocity of the carrier is slow enough when it turns at the decision point to prevent unnecessary lateral forces that could harm or spill a sample.

In many instances, the carrier will be proceeding past the decision point without turning. In these instances, it may not be necessary to update the trajectory and the carrier can continue at its current velocity or even continue to accelerate through the decision point.

If the carrier determines that it needs to turn at the upcoming decision point, the carrier can slow down and initiate the turn at step 526. In some embodiments, the carrier is only capable of forward or backwards movement without assistance. In these embodiments, the carrier or central management controller can communicate with a switching mechanism at the decision point, at step 527, to ensure that any mechanical or electromagnetic devices in the track system 400 are engaged to direct the carrier in the appropriate direction when it traverses the decision point. Examples of devices in the track can include mechanical switches that block one path at a fork and assist the carrier in turning down the other path at the fork (like a railroad switch that can be mounted to rails or a gate when the track is shaped like a trough), magnets that pull the carrier in one direction or another, or changing signaling in the path that assists the carrier in turning, such as an LED that the carrier follows or an LCD or e-ink panel in the track that includes a line that can be followed by the carrier if the carrier is equipped with traditional line-following capabilities. While some embodiments may singulate, scan, and push individual carriers after they stop at a decision point, other embodiments can negotiate a turn before a carrier physically arrives at a decision point. This can allow a carrier to proceed at a velocity limited by the curvature of a turn, rather than having to stop or wait for other mechanisms in order to turn.

In embodiments where a carrier has some steering capability and can turn at a decision point without the assistance of the next internal switch, the carrier can engage its steering mechanism to direct it to the appropriate path upon approaching the decision point. After turning at the decision point (or proceeding without turning) a carrier returns to step 504 to determine its next trajectory.

Maintenance Carriers

While carriers have thus far been often described with respect to transporting samples, it should be understood that carriers are not limited to those that transport samples (e.g. sample carriers). The same mechanisms described with respect to transporting samples may also be used to provide maintenance services to the automation system and the analyzer itself. Traffic on the track of the automation system can include a variety of types of carriers, including sample carriers, maintenance carriers, reagent delivery carriers, and the like.

Maintenance carriers include, but are not limited to, carriers that traverse the automation system and provide maintenance functionality, such as inspecting, calibrating, repairing, diagnosing, cleaning, washing, replacing, replenishing, viewing, documenting, or performing any other suitable maintenance services. Maintenance carriers can use the same motion systems as those used by sample carriers, or may use a different motion system from the sample carriers, provided they are compatible with any tracks that the carriers may share. For example, in some embodiments, maintenance carriers may move responsive to the operation of a friction surface, such as a friction track. In some embodiments, maintenance carriers may move as part of a linear synchronous motor, moving responsive to the operation of electromagnets in the track surface, such as by including magnets in the carrier that are propelled by magnetic interaction with the electromagnets. In some embodiments, the linear synchronous motor may function by operating electromagnets in the carrier.

Furthermore, on a track that provides access to both sample carriers and maintenance carriers, the sample carriers and maintenance carriers may operate with different rules. For example, a sample carrier may be limited in acceleration by the sample it carries and may be required to traverse the track between two stations within a given amount of time. Meanwhile, a maintenance carrier, such as a carrier that inspects the status of track surfaces with a camera, may move more slowly to allow sufficient time to capture images that detail surface conditions.

In some embodiments, maintenance carriers operate on the tracks of the automation system at the same time as sample carriers. In some embodiments, maintenance carriers traverse the track during downtime when there are few or no sample carriers operating on the track. In some embodiments, maintenance carriers can be deployed on demand, which may include moments when sample carriers are operating on the track. For example, a remote diagnostic maintenance carrier may be operated on a track when the analyzer encounters an error or at the beginning or end of a shift as part of routine maintenance. Embodiments of the invention may use on-demand scheduling to ensure that maintenance carriers do not cause unnecessary downtime or impede the paths of sample carriers, including STAT samples. Similarly, a maintenance carrier that operates quickly, such as a carrier that can quickly wipe track surfaces of dust and/or spills as part of the daily maintenance routine, may be suitable for operating on the track as part of normal sample traffic, while sample carriers deliver samples for testing.

In some embodiments, maintenance carriers can be deployed into the automation system for maintenance at the same time that sample carriers transport samples for testing, even if the maintenance carriers move slowly. For example, a maintenance carrier that assists in aligning a pipette may move along a main track to reach a subpath and work with an analyzer station to align the pipette. While the maintenance carrier assists in aligning the pipette, the analyzer station being aligned may be out of order. However, other testing stations may be fully operational and samples can be delivered to those stations. This can assist in providing maintenance to an analyzer while reducing and/or eliminating downtime. By utilizing maintenance carriers that reduce or eliminate downtime, maintenance can be provided on a more regular basis than may have been provided in prior systems. For example, preventative maintenance on pipette alignment can be provided by operating maintenance carriers on the system on an hourly, daily, or weekly basis, without requiring substantial technician involvement or delaying sample testing at other stations.

In conventional systems, maintenance is generally manual and is commonly only provided when an error is encountered. An error can be the result of multiple preventable causes that may have been detected or mitigated had routine maintenance been easily available. For example, an error may occur when components of the system drift out of alignment beyond an operable threshold, preventing a pipette from aligning with a sample. The alignment error can be the accumulation of multiple misalignments of components that have drifted over time.

By providing a simple or routine maintenance, maintenance carriers can be utilized to provide a more robust automation system. Routine use of automation carriers may allow the system to compensate for less robust components, thereby reducing the overall cost of the analyzer and automation system. For example, if an analyzer station utilizes a pipette arm that is not easily adjustable and is made of components that slowly wear or deform, routine observation of the position of the pipette in relation to the automation track can allow an adjustment to the behavior of sample carriers interacting with the pipette in software to compensate for the new alignment. If observation identifies that the alignment has changed, the central controller that controls the motion of carriers can adjust the stopping location of sample carriers that interact with the pipette. That is, what may have been a "misalignment" in a conventional system, may simply be considered a new alignment in some embodiments without causing errors. In this example, the automation system can be made tolerant of defects in pipette alignment without reducing the overall system performance.

In differing embodiments, different maintenance functions can be provided by differing types of maintenance carriers. In some embodiments, a single maintenance carrier can include tools that make it suitable for performing multiple maintenance functions. In some embodiments, multiple types of maintenance carriers are used, each providing specialized tools for differing maintenance functionality. Examples of maintenance functions that may be provided by maintenance carriers in different embodiments include, but are not limited to: inspection of the track, such as by verifying that the track is dust and spill free; calibration of the track, such as by identifying that spills are frequent at a certain point in the track, which can indicate that the cornering speeds being used by the automation system for sample carriers are too high; inspecting elements of the automation system or analyzer, such as by checking the condition of sensors or components; calibrating positions with respect to the automation track, such as by presenting a test pattern to be viewed by external cameras that view the track, allowing them to synchronize image pixels with positions on the track (such as stop points); cleaning the track or sensors accessible to the track; calibrating instruments, such as by providing calibration fluids to verify operation of pipettes or chemistry; pipette alignment; repair and maintenance of elements that interact with the track, such as by replacing disposable pipette tips, or by replacing worn effector pads on robot arms that interact with the track; cleaning elements that interact with the track, such as by cleaning pipette tips and effector pads used by robot arms; and providing remote diagnostic capabilities, such as by allowing a maintenance carriers to be remotely controllable by a service technician (who may be offsite) to visually inspect portions of the analyzer in real-time to diagnose problems encountered during operation of the analyzer.

Figure 9:
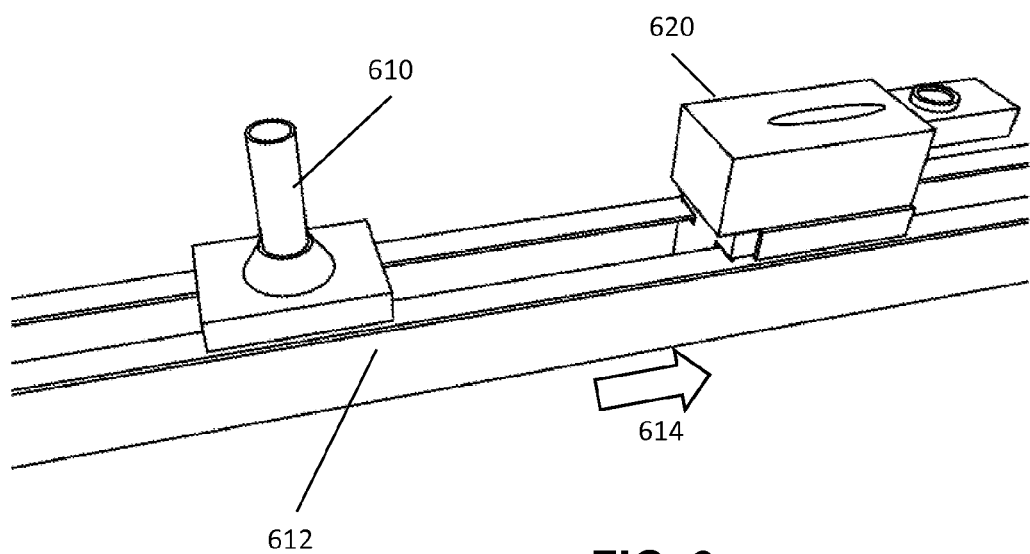
FIG. 9 is a perspective view of an exemplary traffic condition containing maintenance and sample carriers on the same track.

FIG. 9 shows an exemplary traffic pattern along a track in an embodiment of an automation system. Sample carrier 610 and maintenance carrier 620 travel along track 612 in a common direction 614. In this example, carriers 610 and 620 use similar motion hardware that allows both carriers to travel along the same track without colliding. In some embodiments, carrier 620 is capable of moving at substantially the same rate as carrier 610. In other embodiments, maintenance carrier 620 may move slower than the optimal speed of sample carrier 610. Depending on the priority of the sample being transported by carrier 610, this may not greatly affect automation performance, particularly where the maintenance task being provided by maintenance carrier 620 is important and the sample being carried by sample carrier 610 is not a STAT sample.

Figure 10:
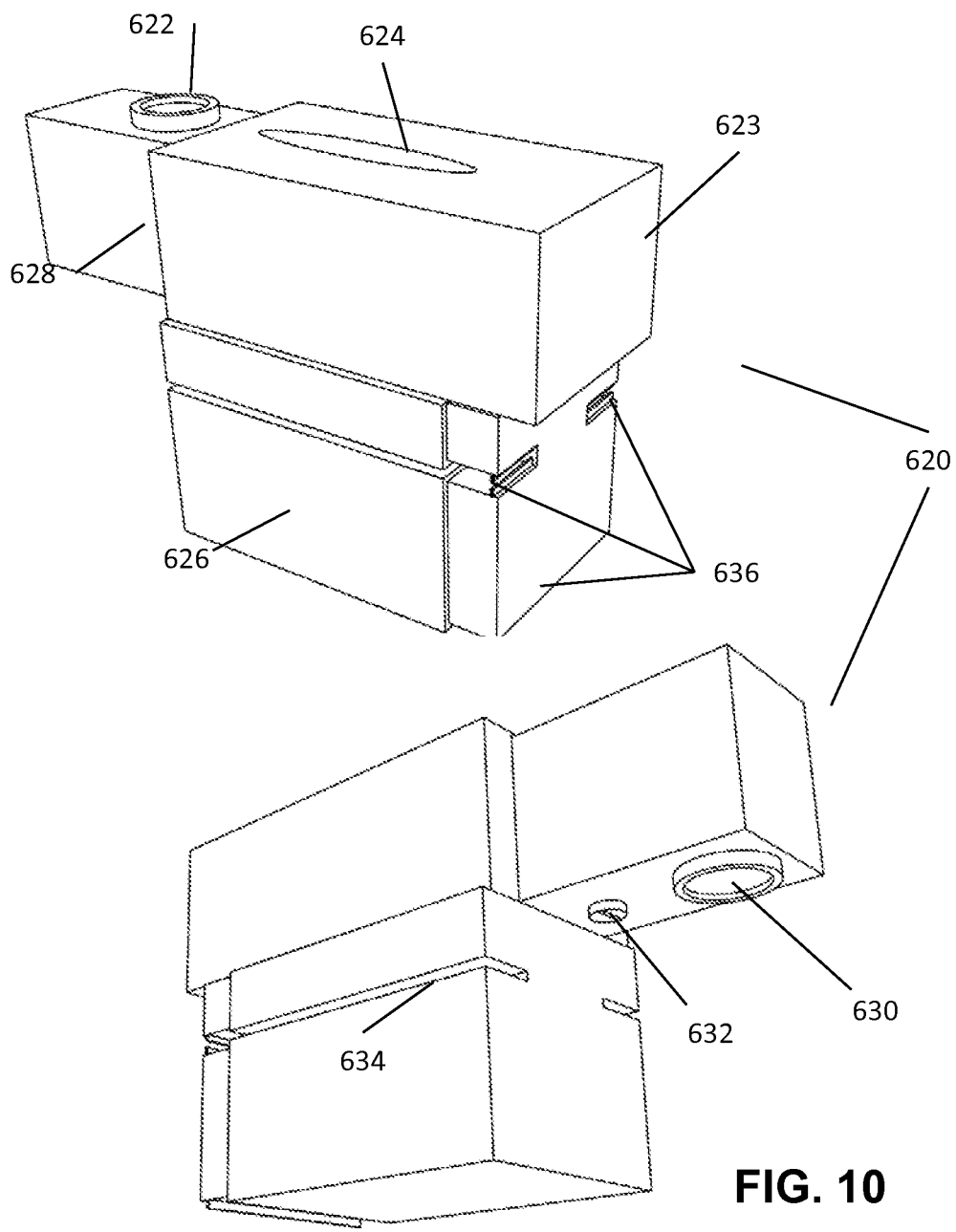
FIG. 10 is a multi-angle perspective view of a multi-purpose maintenance carrier for use with certain embodiments.

FIG. 10 shows two exemplary views detailing the components of carrier 620. Carrier 620 is a multi-function maintenance carrier that provides inspection and cleaning services to the track and overhead pipettes that interact with the track. Carrier 620 includes an upward facing camera 622 that can be used to inspect the condition and status of pipettes. In some embodiments, camera 622 may also be used to align a pipette. By positioning the center of camera 622 at the desired location of a pipette, the image from the upward facing camera can be used to determine the direction and magnitude of any misalignment of the pipette. Recess 624 can be used to provide cleaning and maintenance to a pipette. To clean a pipette tip, the pipette can be lowered into recess 624, where a cleaning fluid may be sprayed onto the pipette to rinse and sanitize the pipette. Recess 624 can allow the cleaning solution to be recaptured by maintenance carrier 620 without spilling cleaning fluid onto the surrounding track. Alternatively, recess 624 may include a bath of cleaning solution into which the pipette may be dipped for cleaning. In some embodiments, a brush, compressed gas, or vacuum may be used inside recess 624 to assist in cleaning the pipette tip.

Maintenance carrier 620 can be provided as a structure having a single continuous housing, or as a multi-component housing divided into separate physical portions. A maintenance carrier can be divided into separate logical portions according to functionality, for example. A maintenance carrier can include a carrier body 626, which can provide an interface with the track and provide propulsion mechanisms to allow the carrier to traverse the track. For example, carrier body 626 may include track guides 634 that interface rails on the track to guide carrier body 626 as it traverses the track. Guides 634 may include low-friction surfaces, wheels, magnets, or any other components suitable to help move and control the carrier body 626 along the rails of the track. In some embodiments, permanent magnets (or electromagnets) in the bottom of carrier body 626 provide a means for magnetic interaction with electromagnets (or permanent magnets) in the track. Electromagnets may be selectively enabled in the track to allow the carrier body to be propelled along the track, thereby forming a linear synchronous motor (LSM). In some embodiments, carrier body 626 may be passive and provide a friction interface for a friction belt that moves carriers along the track. Similarly, in some embodiments, carrier body 626 may include the components described in FIG. 5 with respect to carrier 300. In some embodiments, carrier body 626 is substantially similar to the carrier body used by a sample carrier. For example, some embodiments of maintenance carriers use a carrier body similar to body 260 in FIG. 4A.

In addition to hardware suitable for interfacing a track, a carrier body can also include electronics or mechanisms to assist in traversing the track. For example, a carrier body may include damping hardware to insulate a payload of a carrier from dips and bumps in the track. A carrier body used by a sample carrier may include damping to isolate a sample tube bracket from dips and bumps to prevent shaking or spilling of the fluid sample held by sample carrier. Maintenance carriers may include sensitive electronics or imaging equipment that may be advantageously isolated from dips and bumps to extend the lifetime of the cartridge or image quality. The carrier body may include one or more gyroscopes to assist in providing stability to the carrier.

In some embodiments, one or more tools are mounted onto a sample carrier by using the bracket/tube holder (such as 262 in FIG. 4A) that can otherwise accept a sample vessel. In some embodiments, the carrier body used for maintenance carriers includes a mounting interface to allow multiple tools to be secured to the carrier body. This mounting interface can be a specialized or universal mounting interface to allow multiple types of tools to be made into a common carrier body design. A specialized mounting interface may be suitable for mounting only one type of maintenance tool. A universal mounting interface may be suitable for mounting multiple types of maintenance tools interchangeably. In some embodiments, a universal mounting interface may be suitable for also mounting a sample tube holder or holding a sample tube itself.

A tool portion can be mounted to the carrier body. For ease of reference, the portion of the maintenance carrier that provides tools for maintenance can be referred to as a maintenance cartridge. In some embodiments, the maintenance cartridge is easily removable from the carrier body, while in others the cartridge is securely attached to the carrier body. In some embodiments, the maintenance cartridge is formed integral with the carrier body. In embodiments where the maintenance cartridge is removable, the carrier body can serve as the carrier body for multiple maintenance tasks by changing the maintenance cartridge. Additionally or alternatively, providing a removable maintenance cartridge can allow for disposable or serviceable cartridges that can contain fluids, power, or replacement parts that must be replenished without having to remove or replace the entire carrier. It will be appreciated that the decision whether to make a cartridge removable or permanent (e.g. merely a logical portion of the carrier that provides maintenance tools) may depend on the application. For example, a remotely controllable carrier for inspecting components by a service technician over the internet may be a monolithic carrier with a permanent maintenance carrier, whereas a track maintenance carrier that sprays and wipes track surfaces to keep them cleaned (or lubricated) may be suitable for a replaceable cartridge design whereby the replaceable cartridge includes additional service fluids.

An example of a maintenance cartridge may include portions 623 and 628 (together or separately) of maintenance carrier 620. Cartridge body 623 includes recess 624, as well as cleaning fluids and any necessary spraying/cleaning components for cleaning a pipette using recess 624. Cartridge body 623 may also include a power source, such as a rechargeable battery for operating any of the tools, such as recess 624. In some embodiments, power may be supplied by an onboard power system in carrier body 626.

Cartridge body 623 may support camera housing 628. Camera housing 628 may overhang beyond carrier body 626. This can allow camera 630 to face downward and inspect the track without obscuring its view. In some embodiments, camera housings may extend laterally or transversely to allow alternate views of the track or surrounding components that may not be visible to cameras that are placed on the track coincident with carrier body 626.

Nozzle 632 may be placed on camera housing 628 or cartridge body 623 and allow spray cleaning solution onto track surfaces to clean the track surfaces. Alternatively, nozzle 632 may blow a compressed gas, such as air, to remove dust or debris from the track. The use of nozzle 632 may include uniformly cleaning of the track on a routine basis, or selectively spraying the track in response to soil or spills identified using camera 630. In some embodiments, sponges or squeegees 636 may also be attached to cartridge body 623 to allow any spills or cleaning solution to be cleaned from the track. The combination of nozzle 632 and squeegees 636 may allow carrier 622, act as a robotic mop to keep track surfaces clean and dry. In addition to squeegees 636, sponges or vacuum nozzles may be used to assist in drying track surfaces. For example, if a cleaning solution (such as an ammonia-based cleaner) is residue-free and easily evaporates, squeegees 636 may be appropriate. If the cleaning mechanism is responsible for removing dirt or soil from the track, or uses a cleaning solution that may leave a residue, squeegees 636 may be replaced with a vacuum nozzle.

Cartridge body 623 may also include internal electronics or sensors not shown in FIG. 10. For example, cartridge body 623 may include a processor and controller, wireless transceiver, and inertial sensors. Inertial sensors may allow cartridge body 623 to determine if there are any bumps in the track surface. This information may be relayed to a central controller using the wireless transceiver. Similarly, a wireless transceiver may be used to receive instructions to assist in routing the maintenance carrier and directing the cartridge portion to perform predetermined maintenance functions at certain locations in the automation system. Furthermore, a wireless transceiver may allow real-time video streams from cameras 622 and 630 to be reported to a central controller and/or to an operator. These video streams may also be supplied to a network, allowing remote diagnostics of an analyzer to a technician across the Internet; instructions may be received from the technician via the network to instruct carrier 620 to move and perform maintenance tasks, on-demand.

As can be seen in FIG. 10, maintenance carrier 620 may include multiple maintenance functions, including inspecting, aligning, and cleaning. Maintenance carriers can include carriers that serve multiple maintenance functions or single maintenance functions. For example, a maintenance carrier may include a cartridge body with a pipette cleaning recess similar to recess 624, without providing track cleaning or inspection cameras.

Figure 11:
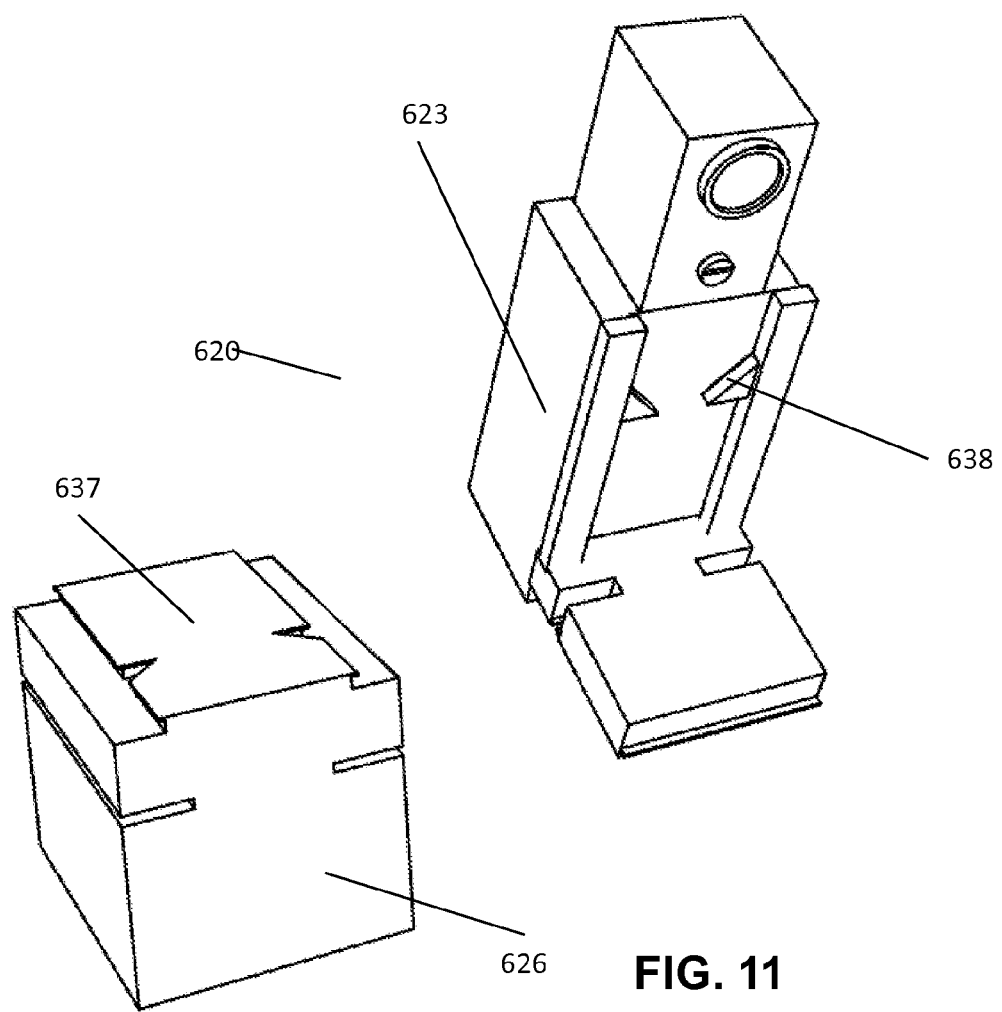
FIG. 11 is a perspective view of a maintenance cartridge and carrier body for use with certain embodiments.

FIG. 11 illustrates an embodiment where maintenance carrier 620 includes a removable maintenance cartridge. Maintenance cartridge 623 may be removed from carrier body 626 and replaced thereon. Mounting interface 637 allows cartridge 623 to be mated to body 626. Tabs 638 allow the cartridge to be secured to the mounting interface. In some embodiments, the mounting interface shares a common design shared with mounting interfaces used by multiple maintenance carriers. A common or universal mounting interface may be provided that allows one or more type of carrier bodies of various designs to be mated to various maintenance cartridges interchangeably. That is, more than one type of maintenance cartridge can share the same mounting interface design. A universal interface design allows carrier body 620 to interface with multiple different types of tools that are included in different maintenance carriers. This can facilitate deployment of different types of maintenance tools into the automation system without having to store redundant carrier components, such as carrier bodies dedicated to each possible maintenance tool.

A mounting interface allows a carrier body 623 to be mounted to a payload, such as a maintenance cartridge 626. Other mounting interface designs that may be suitable for removable attachment include a mechanical clip, mounting holes to allow a cartridge to be bolted to a carrier body, a friction fitting, a magnetic interface to a allow a cartridge to be mounted using magnetic forces, or non-permanent adhesives. Mounting interfaces such as these that provide a removable or reversible mating of a carrier body and payload can be referred to as nonpermanent mounting interfaces. Another example of a nonpermanent mounting interface is a tube holder, such as bracket 262 in FIG. 4A. As noted above, some embodiments of a maintenance carrier may include mating a maintenance cartridge to a sample carrier via the tube holding structure of the sample carrier. In some embodiments, a mounting interface may be a virtual or permanent mounting interface, including molding the carrier body and the payload, such as a maintenance cartridge, out of a single piece of plastic. Other permanent mounting interfaces may include strong adhesives, welds, rivets, or any other mounting mechanism that is not suitable for easy removal.

Figure 12:
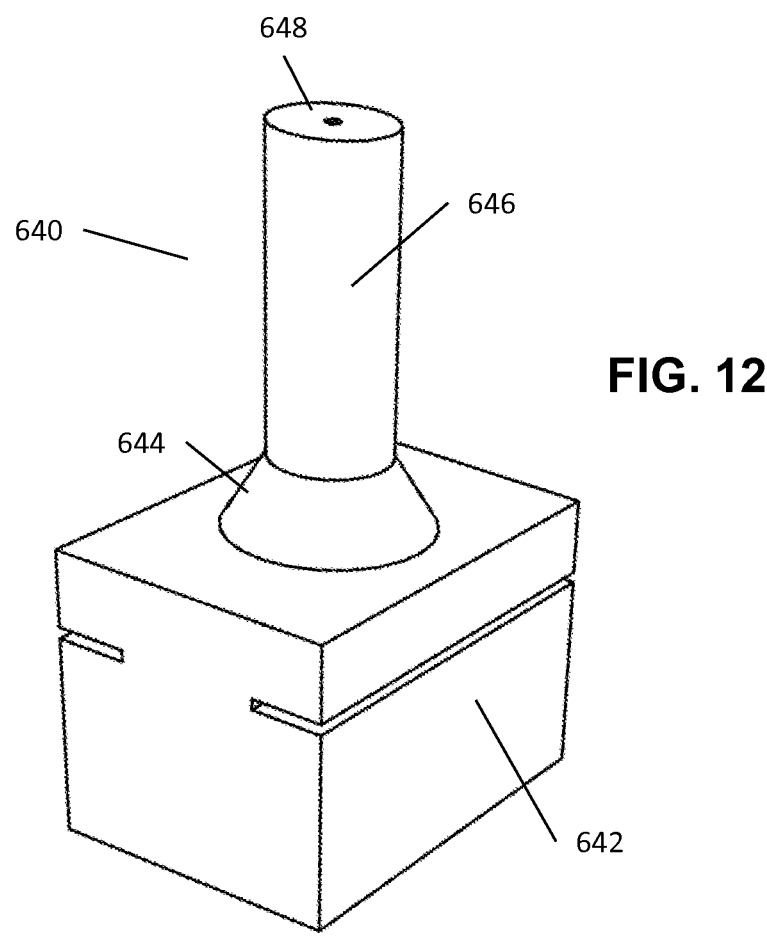
FIG. 12 is a perspective view of a pipette-cleaning maintenance carrier for use with certain embodiments.

FIG. 12 shows an embodiment of a maintenance carrier designed for a single function. Maintenance carrier 640 provides cleaning element 646 for cleaning a pipette. Carrier body 642 may be a sample carrier or a dedicated maintenance carrier body. Bracket 644 may provide a mounting interface for cleaning element 646, which may be shaped like a sample tube. In this example, cleaning element 646 acts as a maintenance cartridge that is placed into a sample carrier to clean pipettes using existing sample carriers. Cleaning element 646 can include a fluid reservoir and brushes. When maintenance carrier 640 is moved to a station having a pipette, a pipette may be inserted into orifice 648 to submerge the pipette into a sanitizing or cleaning solution contained in cleaning element 646. Brushes surrounding orifice 648 at the top of cleaning element 646 may be used to physically wipe off any excess cleaning solution or particulate matter that has accumulated on the pipette. By deploying maintenance carrier 640, routine cleaning of sample handling pipettes may be effectuated with little or no operator involvement. Because the effort needed to use maintenance carrier 640 is minimal, carrier 640 may be used without interrupting the normal workflow in the IVD environment and may require no additional training of laboratory personnel. This allows frequent and routine cleaning of pipettes to ensure that all testing stations use clean pipettes when handling samples.

Figure 13:
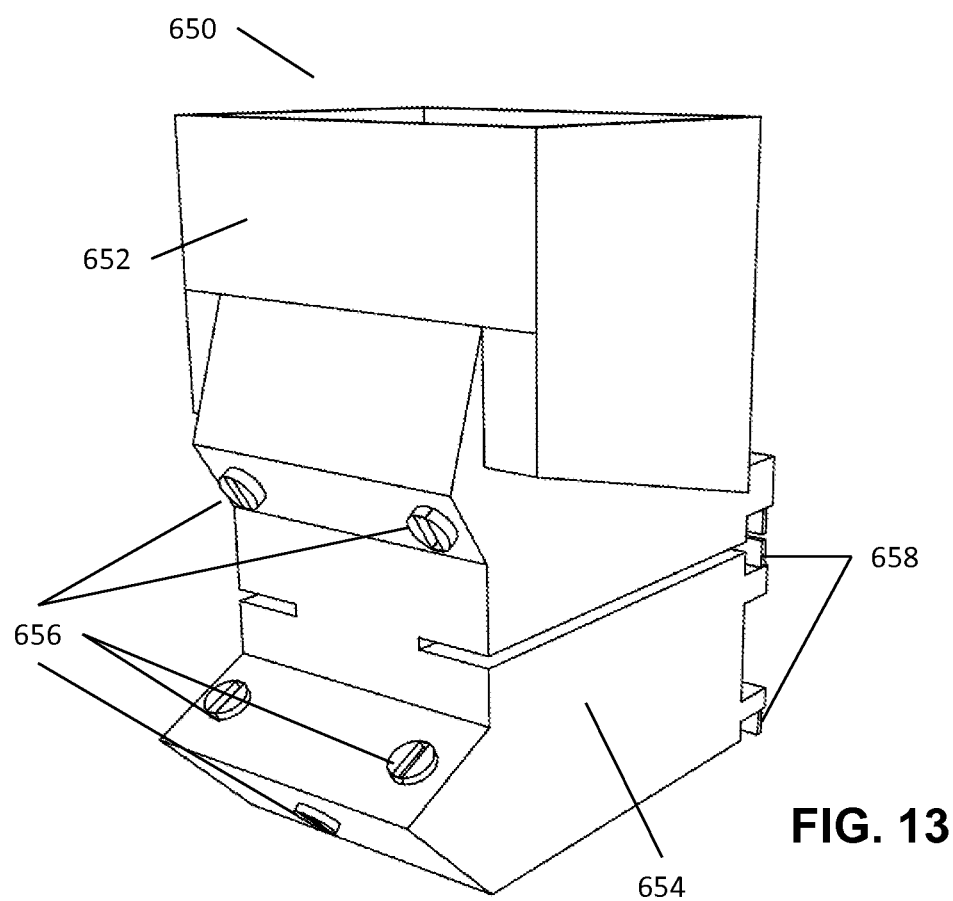
FIG. 13 is a perspective view of a track-cleaning maintenance carrier for use with certain embodiments.

FIG. 13 shows another embodiment of a maintenance carrier 650.

Maintenance carrier 650 is designed to clean and dry multiple track surfaces of a track, such as track 612 of FIG. 9. Carrier 650 is illustrated as having a monolithic/integral structure that includes both the carrier body 654 and tools used to clean the track 652, 656, and 658 as part of the overall structure of the carrier. In some embodiments, carrier 650 includes a carrier body and separate maintenance cartridge that includes a reservoir, nozzles, and squeegees. Nozzles 656 are aimed at top and bottom track surfaces, including substantially all surfaces that guide carriers along the track. Squeegees 658 allow the cleaning solution sprayed by nozzles 656 to be removed or to provide a scrubbing action to further clean the surfaces. Reservoir 652 may be a replaceable or refillable reservoir that contains a cleaning solution to be sprayed by nozzles 656. Maintenance carrier 650 may be suitable for regular deployment to ensure that all surfaces are cleaned a regular intervals.

As shown in FIG. 14, maintenance carrier 660 includes a plurality of inspection cameras that may be used for remote diagnostics of the automation system and/or any elements of the analyzer that are viewable from the automation track. Upward facing camera 662 may be used to inspect elements above the track, such as pipettes and sample handling arms (e.g. pick and place arms). Upward facing camera 662 may also be used to assist in aligning sample handling arms or pipettes. Sideways facing cameras 664 may be used to inspect sidewalls of the automation track. In some embodiments, the sidewalls may contain position encoding information or sensors that detect the presence of carriers. Sideways facing camera 664 may be useful for determining if there is any damage to the track position encoding or any damage to sensors in the track walls. One or more track surface facing camera 666 can be used to inspect the condition of the top and bottom surfaces of the track that may be used to guide the carrier. This inspection may be useful in determining whether the track has been damaged and may be useful in determining where spills are occurring, and the cause of these spills, such as bumps in the track.

Maintenance carrier 660 may be of suitable design for use as a remote diagnostic robot. An operator may communicate with carrier 660 to instruct the carrier to inspect certain locations in the analyzer. In turn, carrier 660 may follow the directions of the operator and send back real-time video streams (or still photos) that may be used by the operator to determine the status of the various components in the analyzer and automation systems. This can assist the operator in diagnosing and/or fixing any problems that may be encountered. Similarly, the operator may use the remote diagnostic capabilities to perform preventative inspections to verify that the systems in the analyzer appear to be working properly. The operator may be a local technician in the laboratory having the analyzer or may be a technician that interacts with carrier 660 across a data network, such as the Internet. Conventional networking infrastructure may be used to facilitate this communication, such as switches, routers, gateways, firewalls, VPNs, TCP/IP networks, and the like.

FIG. 15 shows another embodiment of a maintenance carrier suitable for use as a remote diagnostic robot. Like maintenance carrier 660, maintenance carrier 670 includes an upward facing camera 672. Maintenance carrier 670 also includes one or more track facing cameras 678, which may be angled to provide alternate views of track surfaces, including track walls and horizontal surfaces. Whereas cameras are integrated into the structure of the carrier body of carrier 660, carrier 670 has a less integral structure. A camera cartridge 675 can be mounted to a carrier body 674, using a mounting plate 676. Mounting plate 676 includes holes suitable for joining maintenance cartridge 675 to carrier body 674 using screws, for example.

It should be appreciated that any embodiments illustrated as having distinct carrier bodies and distinct maintenance cartridge components can also be implemented in an integral manner, like that shown in FIG. 14. Similarly, any embodiments illustrated as having a uniform structure that includes logical sections or components of a maintenance cartridge (such as tools integrated into the physical structure of the carrier body) may also be implemented as having separate and distinct maintenance cartridges that utilize a mounting interface, such as mounting plate 676 or mounting interface 637.

Figure 16:
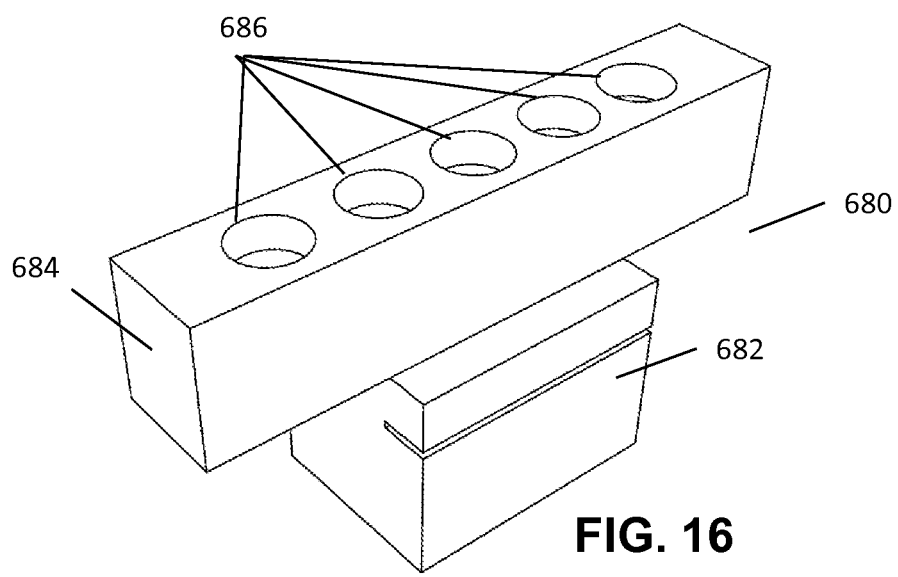
FIG. 16 is a perspective view of a calibration maintenance carrier for use with certain embodiments.

FIG. 16 shows an exemplary embodiment of a calibration maintenance carrier 680. Maintenance carrier 680 includes a carrier body 682 for transporting a plurality of calibration fluids in maintenance cartridge 684. Maintenance cartridge 684 may include a plurality of reservoirs 686 that may include one or more types of fluid that may be used for calibrating fluid handling equipment that interacts with the automation system. For example, reservoirs 686 may include calibration reagents suitable for performing calibrated clinical chemistry tests. Similarly, reservoirs 686 may include fluids of calibrated viscosities or specific gravities that may be used to calibrate the suction efficiency of various pipettes that interact with samples on track. Other examples of calibration fluids may include dyes or fluids of known salinity, viscosity, gravity, dye color, etc. The selection of suitable fluids for use with maintenance cartridge 684 depends on the type of calibration test that a person of ordinary skill in the art selects to use with maintenance carrier 680.

Carrier 680 may also be a cleaning maintenance carrier. Cleaning solutions may be placed in reservoirs 686 and a pipette may be cleaned by interacting with each adjacent reservoir in succession starting with the most caustic solution at the front of the carrier, followed by rinsing reservoirs and sanitizing fluids. The fluids may be selected and laid out to allow harsh chemical cleansing agents to clean the pipette while rinsing these agents during the process.

Figure 17:
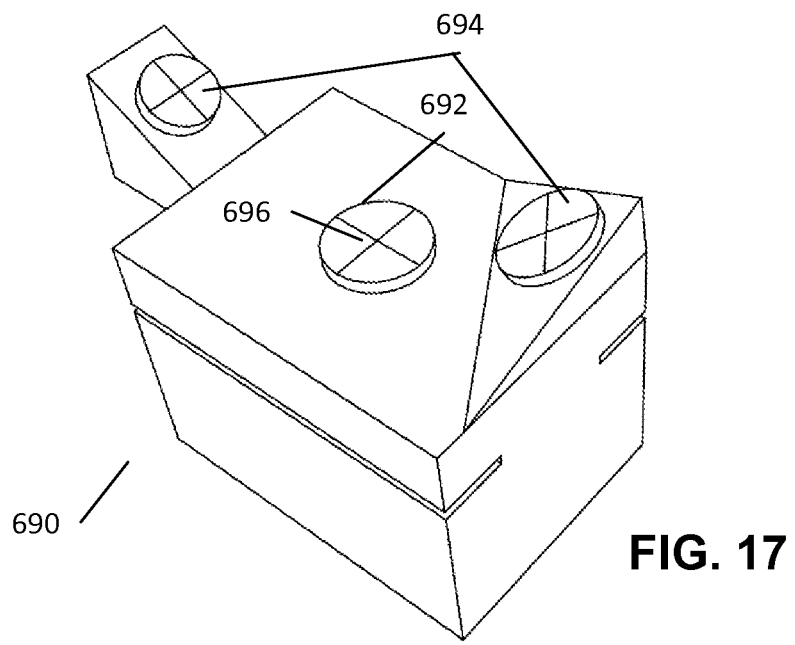
FIG. 17 is a perspective view of a calibration maintenance carrier for use with certain embodiments.

FIG. 17 illustrates a precision alignment maintenance carrier 690.

Maintenance carrier 690 includes a plurality of upward facing cameras 694 and 692. These cameras may include etched reticles 696 that have been carefully aligned on the optics of the camera to provide positioning information in the image. For example, upward facing camera 692 may be placed precisely underneath the expected location of a pipette. Reticle 696 may provide visual cues in the image to determine the degree and magnitude of any misalignment of the pipette. Cameras 694 may be angled and have reticle information that allows any skew or height alignment issues with the pipette to be identified and quantified. In this manner, a simple snapshot of each pipette the automation system can be created by the maintenance carrier 690 and can include all of the information necessary for a technician to determine whether a pipette is beyond the tolerance for alignment and to determine the specific changes needed to bring the pipette back into alignment.

The embodiments illustrated in FIGS. 10-17 illustrate a subset of possible maintenance carrier designs. Maintenance carriers may include one or more tools suitable for performing a maintenance operation. For example, maintenance carrier 620 includes the following tools: cameras for providing an inspection maintenance operation on the track and elements of the analyzer; a recess suitable for performing a cleaning maintenance operation on a pipette; and a nozzle and fluid reservoir, along with squeegees, to provide a cleaning maintenance operation on the track. Carrier 640 includes a pipette cleaning tool for providing a pipette cleaning maintenance operation. Carrier 650 includes fluid reservoir, nozzle, and squeegee tools for providing a track cleaning maintenance operation. Carrier 660 includes a plurality of cameras as tools for providing inspection maintenance operations. Carrier 670 also includes, a plurality of cameras as tools for providing inspection maintenance operations. Carrier 680 provides a plurality of calibration fluid reservoirs 686 as tools for providing a calibration maintenance operation. Maintenance carrier 690 provides a plurality of cameras and reticles for providing inspection and alignment maintenance operations. A maintenance carrier can cooperate with, interact with, or assist other elements in the automation system or analyzer to achieve the maintenance operations. Accordingly, providing a maintenance operation can be construed broadly to include embodiments whereby other elements work with the maintenance carrier to provide the operation.

Examples of tools that may be included in a maintenance cartridge for providing a maintenance operation include sensors (such as cameras that inspect elements of stations served by the automation system, the alignment of pipettes that access the automation track, the track condition, or the status of sensors or lenses that are built into the track). These sensors can provide inspection, alignment, observation, or calibration maintenance operations.

Cleaning maintenance operations may be provided by one or more cleaning tools, such as cleaning heads. For example, cleaning element 646 may be referred to as a cleaning head that serves to clean pipettes that can access the track. Carrier cartridge 623 in FIG. 10 includes recess 624, nozzles 632, and squeegees 636, which may all work as cleaning tools for cleaning track surfaces and pipettes that can access the track. Maintenance carrier 650 includes a plurality of nozzles and squeegees that may act as a cleaning head or cleaning services of the track. Other cleaning tools that may be used to provide a cleaning, maintenance, operation include a compressed gas that may be used to blow dust or debris from surfaces being cleaned. This compressed gas may be in the form of a refillable cylinder, such as a CO2 cartridge, or may be provided by a bellows or piston as part of the maintenance cartridge. Vacuums, brushes, sponges, squeegees may also be provided as cleaning tools for performing a maintenance operation. A cleaning solution reservoir or spray nozzles may also act as a tool for providing cleaning operations.

Calibration operations may be provided by various calibration tools. A calibration tool may include a reservoir of a calibration fluid, such as shown in FIG. 16. In addition, a calibration tool may include a test pattern or target that is carried by a maintenance carrier to be presented to optical sensors within the automation system to assist in calibrating those optical sensors. For example, a reticle may be provided on the side of a maintenance carrier or the top of the maintenance carrier to provide frame of reference to cameras that are observing the track during an alignment maintenance procedure designed to align those cameras.

Other maintenance tools may include sensors that detect acceleration experienced by a maintenance carrier, such as solid-state accelerometers, gyroscopes, solid-state compasses, or the like, that may be used to provide a track calibration operation, whereby track sections may be tested to be free of bumps and suitable track speeds around corners may be determined. Furthermore, alignment operations may be provided by mechanical sensors, such as capacitive pressure sensors that detect the location of a pipette relative to a surface of a maintenance carrier. Similarly, chamfered holes may allow mechanical alignment of the pipette inserted into the hole.

Repair tools may be provided to perform repair maintenance operations. For example, a maintenance carrier may include a plurality of spare parts for elements of the analyzer that are easily replaceable. For example, a maintenance carrier may include a tool that is capable of removing worn effector pads for robot arms that are used in a pick and place sample handling station. That tool may be further configured to replace the worn effector pads from an onboard store of new effector pads. Similarly, a tool as part of a maintenance carrier may be configured to remove a replaceable pipette tip and replace the pipette tip with a new tip.

Maintenance carriers can include communication systems as part of the maintenance cartridge or as part of the carrier body. The communication system may allow the maintenance carrier to receive instructions from an operator regarding deployment and execution of maintenance operations. The communication system may also provide real-time data, such as sensor data and live camera feeds. In some embodiments, this data and image information is stored in memory onboard the carrier, rather than transmitted. The memory that stores this information can later be accessed by an operator or the system to automatically analyze the recorded data as part of a maintenance operation, such as inspection. The communication system may also provide two-way communication that allows real-time control of the maintenance carrier by a computer or by an operator to allow the maintenance carrier to explore the automation system, locate problems, and provide maintenance operations to solve these problems.

Maintenance operations may use a processor to make determinations, execute instructions, or analyze collected data. This processor may be part of a central processor for the analyzer, onboard the maintenance carrier, or any combination thereof. For example, a processor may take observed data about a pipette and calculate the amount of misalignment of the pipette and may further calculate an offset to correct for the misaligned pipette. An onboard processor or central processor can determine the current location of that maintenance carrier. Real-time location information of a carrier may be useful for determining where and whether to perform a maintenance operation using the carrier. An onboard processor of the maintenance carrier may execute received or stored instructions to facilitate execution of a maintenance operation by any maintenance carrier. The processor may also be involved in recording and collecting data from maintenance carrier sensors.

Benefits of using maintenance carriers can include reduced downtime of an analyzer. For example, preventative maintenance may reduce the risk that catastrophic failure will occur that necessitates a full shutdown of the analyzer while a technician repairs the problem. Furthermore, some maintenance operations that may have required a full shutdown and manual execution in the prior art may be fulfilled by maintenance carriers that are capable of performing the maintenance while sample carriers continue to traverse the automation system. For example, in some prior art systems, alignment procedures are typically done manually, requiring the system to be shut down while a technician follows manual alignment procedures. In some embodiments, alignment maintenance carriers may be deployed to observe the alignment of pipettes on a regular basis without disrupting the flow of samples. This information can be analyzed without stopping the operation of the analyzer to determine whether the alignment errors need to be mitigated.

Another benefit of maintenance carriers is that some embodiments can utilize the same infrastructure as that used by sample carriers to reduce the cost of providing automated maintenance of the system. For example, the same carrier motion systems may be shared between maintenance carriers and sample carriers. For example, the same motive mechanisms can be used to propel maintenance carriers as those used by sample carriers. Sample carriers and maintenance carriers can share the same tracks. Therefore, in some embodiments, the additional cost of adding a maintenance carrier to the system is not substantially greater than the cost of adding an additional sample carrier.

In some embodiments, by automating maintenance operations, seemingly complicated maintenance tasks can be performed by carriers, rather than by technicians. This can allow maintenance to occur without requiring that operators learn new procedures or skills. This may allow less skilled personnel to manage analyzers without the need for special training or expensive technician visits.

Maintenance Carrier Auto-Loaders

While individual carriers can be useful for performing specific maintenance functions, groups of carriers can provide a more powerful suite of maintenance functions. Furthermore, the maintenance carriers that are automatically deployed can provide maintenance without requiring an operator to actively participate in the maintenance function. When maintenance carriers are automatically deployed, routine maintenance can occur even when no operator is present or without requiring an operator to follow a rigorous maintenance schedule. It should be appreciated that in some embodiments, maintenance carriers can be deployed automatically in response to an event, a schedule, or a request by an operator (who may be local or remote over the Internet).

Figure 18:
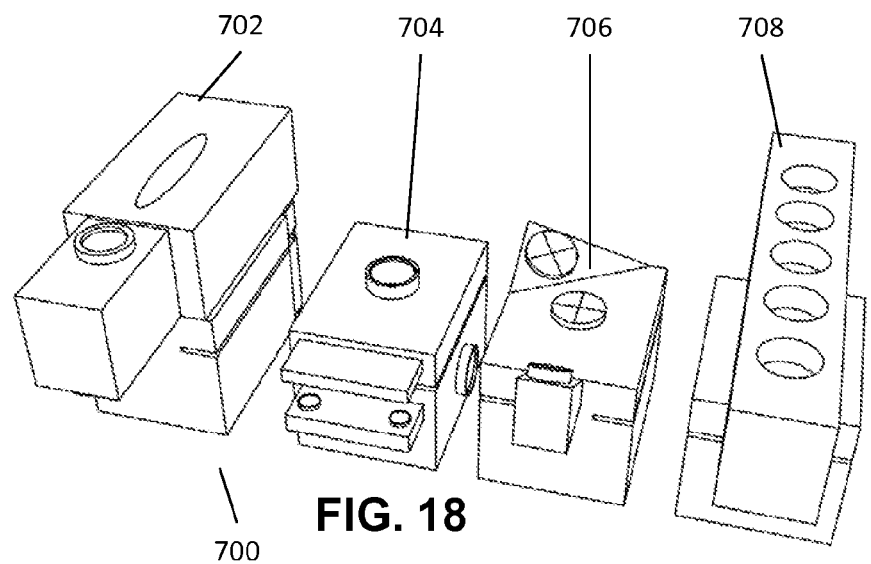
FIG. 18 is a perspective view of a group of maintenance carriers.

FIG. 18 shows a group of maintenance carriers 700. This group includes a cleaning and inspection maintenance carrier 702, an inspection carrier 704, an alignment carrier 706, and a calibration carrier 708. The selection of these carriers is illustrative and other carrier groups can include multiple instances of each maintenance type, as well as any number of additional maintenance carrier types. In some embodiments, the group of available maintenance carriers may be more or less diverse than group 700. A group of carriers 700 may be stored at a location in the analyzer, allowing individual carriers to be deployed when needed. Carriers from a group 700 can be selected on-demand or according to a schedule to perform maintenance tasks. The carrier selected from group 700 can depend on the maintenance task needed. Similarly, the frequency with which members of group 700 are selected can vary depending on the maintenance task. For example, alignment carrier 706 may be deployed as part of an initial setup of the analyzer or new stations and later deployed on an infrequent basis when an alignment error is detected or periodically, such as every two weeks. Meanwhile, track cleaning carrier 702 may be deployed more frequently, such as hourly or daily, to ensure that the track remains clean. Similarly, inspection carrier 704 may be deployed only when errors are detected and may be used to provide remote diagnostics via service technician over the Internet. Calibration carrier 708 may be deployed at regular intervals, such as after a set number of samples have been handled by a station, to allow frequent calibration of pipettes.

It should be appreciated that different maintenance carriers need not share the same form factor. Maintenance carriers may be of varying sizes with a form suitable for the function of the maintenance operation to be performed. Carriers may share a common track interface and at least some common features that allow the carrier to be placed onto a track. In some embodiments, maintenance carriers share a common width that allows a robot arm to easily handle different types of maintenance carriers. In some embodiments, carriers share a common physical feature that allows a single auto-loader to grip multiple types of maintenance carriers.

Figure 19:
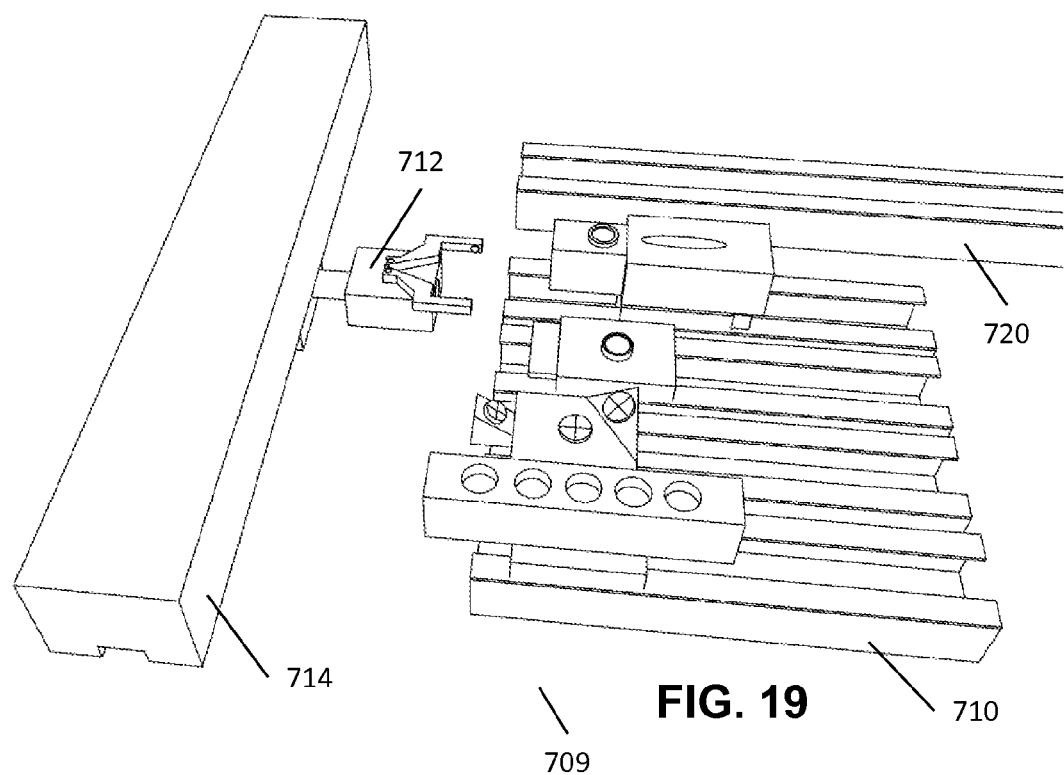
FIGS. 19-21 are perspective views of an auto-loader during the deployment of a maintenance carrier.

FIG. 19 shows an exemplary embodiment of an auto-loader 709 for selectively deploying individual maintenance carriers. Like the group of carriers in FIG. 18, maintenance carriers in FIG. 19 may be arranged in a group. A group of carriers may be stored in a storage area, such as rack 710. The content and arrangement of storage rack 710 may be selected based on the available maintenance tasks to be provided. In some embodiments, certain carriers are disposable or may require multiple carriers to be deployed at any given time. Accordingly, multiple instances of a maintenance carrier may be provided in storage racks 710. In some embodiments, storage rack 710 provides an array of maintenance carriers that may be accessed in parallel. In some embodiments, storage rack 710 provides more than one maintenance carrier per position in an array, such as multiple instances of the same type of maintenance carrier. These maintenance carriers may then be dispensed in a serial manner on demand.

A robot arm, such as arm 712 may selectively engage carriers in storage rack 710. A robot arm 712 may move along track 714 to individual positions in storage rack 710. This allows robot arm 712 to select individual carriers for deployment. Once robot arm 712 has selected a carrier, the carrier may be placed onto a track, such as track 720 which may feed into a main track of the automation system. Track 720 may act as a bidirectional import or output track to allow maintenance carriers to be deployed into the automation system and removed therefrom. Alternatively, separate input and output lanes may be provided to load and unload maintenance carriers onto the main track of an automation system.

Figure 20:
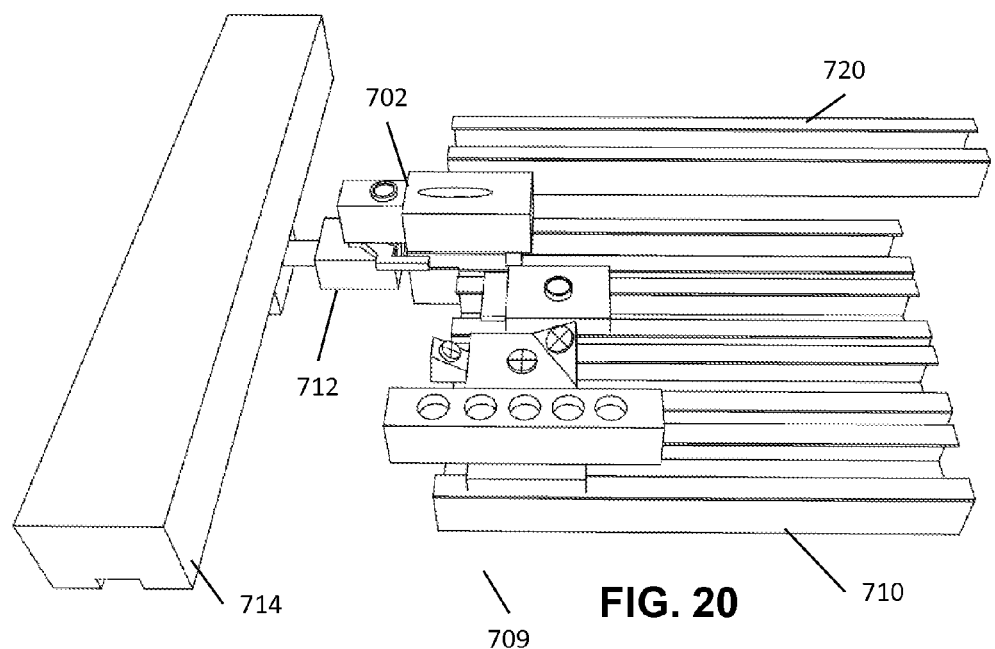
Figure 21:
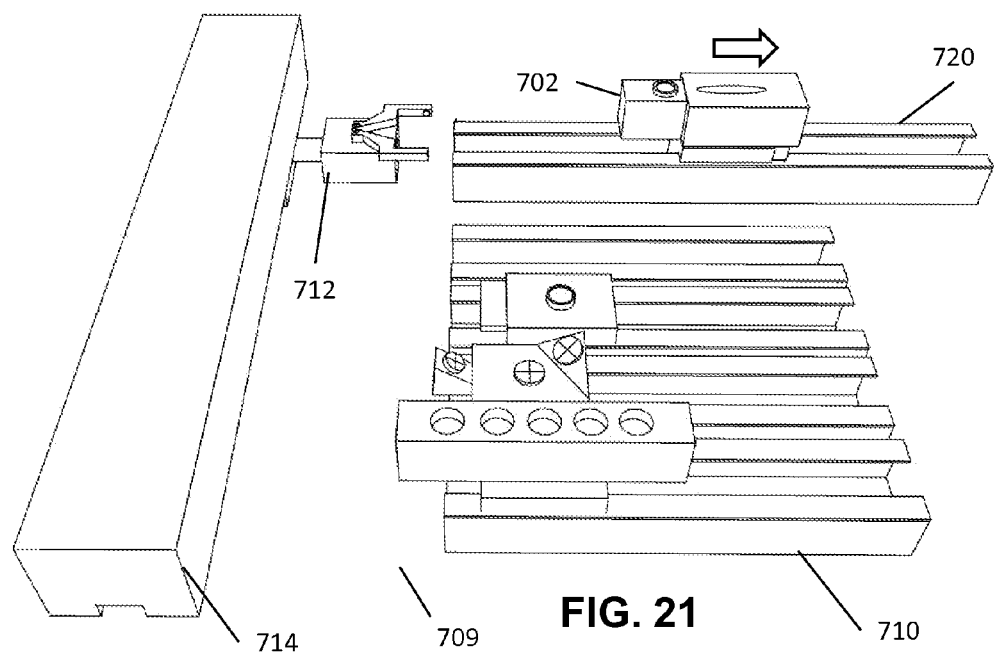

In the example shown in FIG. 19, robot arm 712 aligns with a cleaning maintenance carrier stored in storage rack 710. At a shown in FIG. 20, robot arm 712 removes the cleaning maintenance carrier 702 from rack 710. As shown in FIG. 21, robot arm 712 then aligns with track 720 and deploys maintenance carrier 702 into the automation system.

When maintenance carrier 702 completes a maintenance task, maintenance carrier 702 may be returned to storage via track 720. Robot arm 712 may then remove maintenance carrier 702 from track 720 and place the maintenance carrier back into a rack 710. Robot arm 712 can be controlled by a processor that is part of the auto-loader system or by a processor that is integrated with the other systems of the analyzer. The processor controlling the robot arm 712 can be in communication with the other systems of the analyzer or a central controller of the analyzer, allowing the auto-loader to coordinate deployment of maintenance carriers with the remaining systems in the analyzer.

Other types of robot arms may also be used. Whereas robot arm 712 moves along the track to adjust its position, robot arms having articulated joints may also be used. Pick and place arms, plungers, actuators, pneumatic devices, or forking track sections may also be used to selectively deploy and store maintenance carriers. In some embodiments, track sections are used without the need for a robot arm. In these embodiments, the track sections or the maintenance carriers may provide motive forces to selectively deploy the carriers. For example, the central controller may initiate a deployment by communicating with a maintenance carrier. The maintenance carrier may then travel along the track onto the main track and deploy itself. Later, the maintenance carrier may be instructed to leave the main track and return it to a storage location.

The auto-loader may also be used beyond simply deploying and storing carriers. For example, carriers may need to be recharged or have payloads replenished. For example, wherein the carrier has active components and includes an onboard power source, such as rechargeable batteries, the auto-loader may provide one or more recharging stations to recharge maintenance carriers while they are stored. For example, in FIG. 19, the rails of storage rack 710 may include electrical contacts to allow storage rack 710 to recharge onboard batteries of the maintenance carriers stored therein.

Similarly, where carriers include fluids, such as calibration fluids or cleaning fluids, these fluids may be replenished while the carriers are stored in the auto-loader. For example, maintenance carrier 702 may include a cleaning solution that is sprayed onto pipettes and/or the track while it performs maintenance operations. This cleaning solution may be replenished by refilling an onboard reservoir while the maintenance carrier is in storage racks 710. In some embodiments, the cleaning solution is available in disposable cartridges. When a maintenance carrier has completed a maintenance operation, an old cartridge may be removed from the maintenance carrier while in storage racks 710. Subsequently, a fresh cleaning solution cartridge may then be installed in the maintenance carrier. Similarly, maintenance carrier 708 may include disposable cartridges having calibration fluids. These cartridges may be replaced while the maintenance carrier is stored in the auto-loader. The spent cartridges may then be disposed of into a waste receptacle automatically by the auto-loader, stored for later recycling or replenishment, or replenished by the auto-loader.

It should be appreciated that in some embodiments, the auto-loader may be used to attach and remove maintenance cartridges from carrier bodies without removing the entire carrier from the automation system. For example, an embodiment of an auto-loader may have access to an automation track or a sidecar where carriers may stop. An exemplary auto-loader can select an appropriate maintenance cartridge to attach to the carrier to perform a maintenance task. When the task is completed or the cartridge is exhausted, the carrier can return to that part of the track to allow the auto-loader to remove the cartridge from the carrier, allowing the carrier body to receive other cartridges. In some embodiments, the carrier body may also be configured to receive sample vessels after a maintenance cartridge is removed.

The recharging and replenishing steps may occur automatically in the auto-loader. Storage rack 710 may include sensors sufficient to detect when charge levels or fluid levels are low and automatically replenish or recharge the carriers. By providing automatic recharge and replenishing, an operator can operate the analyzer without actively having to maintain the maintenance carriers themselves. Instead, an operator may merely need to periodically restock fluids. In some embodiments, the operator may not need to worry about charge levels of carriers because maintenance carriers are automatically recharged.

Other tasks that may be automatically provided by an auto-loader, include replenishing repair items that are stored in repair maintenance cartridges. For example, a maintenance carrier that replaces effector pads may have a stock of effector pads that is periodically refreshed by the auto-loader when the carrier is stored in storage racks 710. A maintenance carrier that includes replacement tips for pipettes may have the stock of replacement tips refreshed when a maintenance carrier is stored in storage racks 710.

The auto-loader may provide automatic deployment and maintenance of maintenance carriers by interacting with a central controller of the analyzer. The central controller of the analyzer may send specific maintenance requests to the auto-loader. In some embodiments, certain tasks, such as recharging, are done automatically by the auto-loader without the need for instruction from another controller. In some embodiments, the auto-loader operates with minimal instruction from a central controller. For example, in some embodiments, the auto-loader detects low fluid levels in the carrier and automatically replenishes these fluids. In some embodiments, the maintenance carriers themselves detect the status of onboard fluids and report this information to the auto-loader or a central controller. Then, the central controller or the auto-loader will take appropriate action. If the status of the maintenance carrier is reported to a central controller, the central controller may then communicate a request for replenishing fluids to the auto-loader. If the status of the maintenance carrier is reported directly to the auto-loader, the auto-loader may replenish fluids without the need to interact directly with the central controller to receive the instruction.

The auto-loader many detect the inventories of replacement fluids or other items and report this information to the operator. For example, when fluid cartridge levels or fluid reservoir levels in the auto-loader are low, the auto-loader may report to the operator (via a warning message) that the operator needs to replace the store of cartridges or refill a fluid reservoir.

Figure 22:
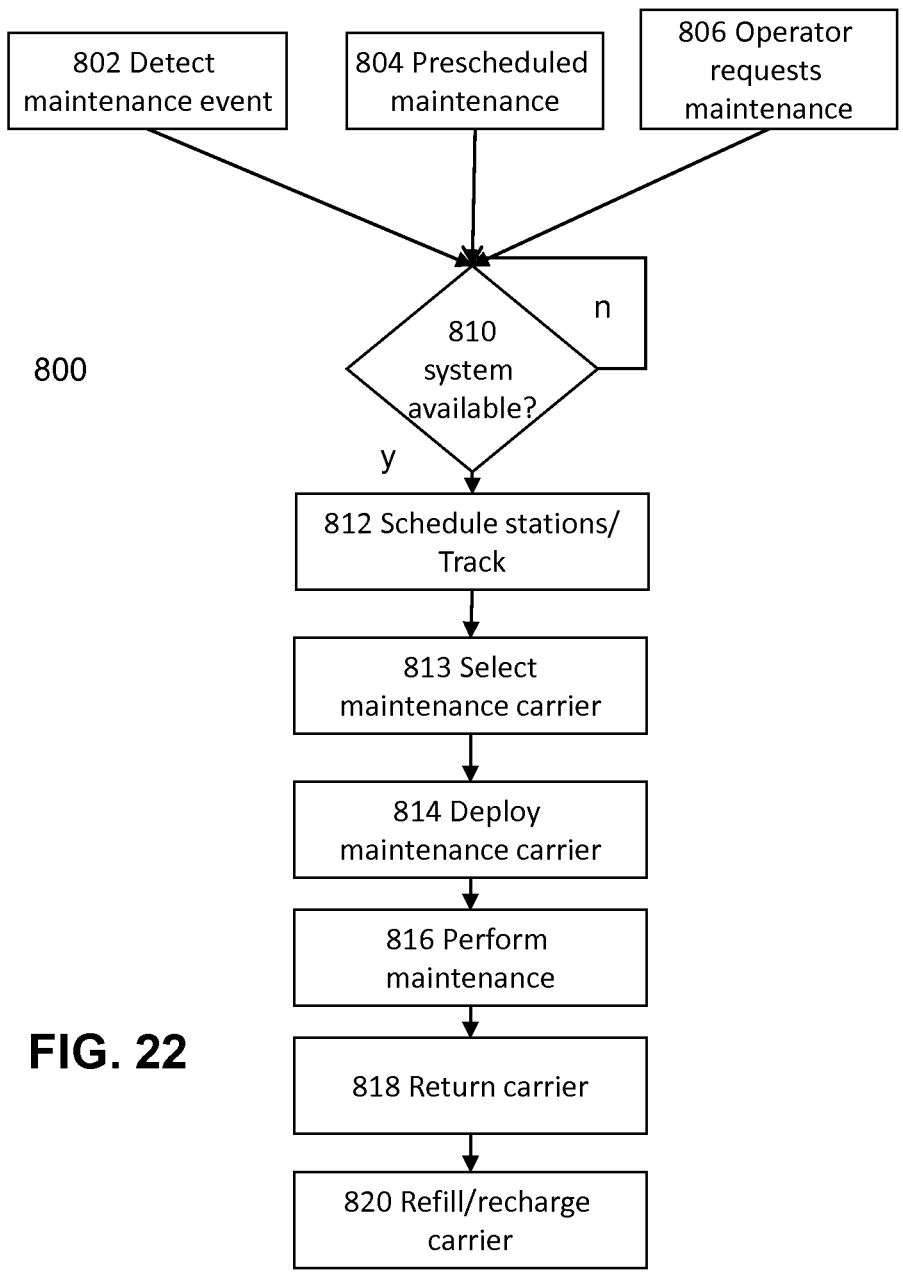
FIG. 22 is a flow chart demonstrating a maintenance operation.

FIG. 22 presents a flow chart of a maintenance process 800 when using an auto-loader. Maintenance process 800 can be controlled by one or more processors, such as a central controller that schedules sample assays. There are three primary ways to begin a maintenance process. Certain maintenance processes are event or condition driven. For example, if an alignment error is detected with the pipette, a maintenance carrier can be deployed on demand. This type of maintenance process begins at step 802. At step 802, a maintenance event is detected. For example, a spill can be detected or an alignment error or other type of error can be detected by any number of sensors in the analyzer. Certain maintenance processes, such as routine track cleanings, can be scheduled. For example, in some embodiments track maintenance can be scheduled for the end of each shift of an operator. Scheduled maintenance begins at step 804. At step 804, a schedule is monitored by a processor, such as a central controller and started automatically according to the schedule. Certain processes are user controlled. An operator can request that a maintenance operation occur. For example, the operator may select a maintenance operation via a terminal that controls the analyzer and/or the automation system. At steps 802 through 806, the processor determines a maintenance operation to perform in response to the current conditions or requests. In a scheduled or requested maintenance operation, the schedule may define the operation to perform. In an unscheduled operation, at step 802, the processor may determine an appropriate maintenance operation to respond to the detected condition. When the scheduled time occurs, the maintenance process can begin.

At step 810, the processor that handles the maintenance process 800 determines if the system is ready for maintenance. For example, it may be undesirable to perform a slow track-cleaning that may block STAT samples that are in process. Step 810 allows the system to determine the precise moment when maintenance is appropriate based on current conditions with the analyzer and allows maintenance to be performed without interfering with normal sample analysis and operations of the analyzer. If the processor determines that it is not an appropriate moment to deploy a maintenance carrier, step 810 can repeat until the system is available for maintenance.

At step 812, when the analyzer is ready for a maintenance operation, the central processor schedules the maintenance. This step can include coordination with affected stations to ensure that they are prepared and are not in-use when the maintenance carrier arrives. For example, if a maintenance process involves verifying the alignment of a pipette at a station in the analyzer, the central scheduler will coordinate with the station having the pipette such that the station will be ready for maintenance at a predetermined time when the maintenance carrier is scheduled to arrive at the pipette. Similarly, because sample carriers may still traverse the automation system during some maintenance operations, the processor coordinating the maintenance can coordinate with track resources to prevent introducing a maintenance carrier in the area of a sample carrier to avoid collisions of carriers. It should be appreciated that the processor or processors coordinating maintenance operation 800 may view track sections and stations in the analyzer as resources that can be scheduled. The processor can then schedule the needed resources to be available for use by the maintenance carrier being deployed.

At step 813, an appropriate maintenance carrier is selected from a storage rack to perform the maintenance operation. For example, if an alignment operation is needed, the processor can automatically select a carrier that is equipped with the appropriate tools to perform the operation. At step 814, a maintenance carrier suitable for the maintenance task is deployed automatically under the control of the processor. This deployment can be done via an auto-loader as discussed above. At step 816, the deployed maintenance carrier traverses the automation system and performs the maintenance task. For example, the carrier may clean the track by traversing the entire automation track while operating cleaning head or a carrier may participate in the alignment of a pipette by moving to the location of the pipette and performing an alignment operation.

At step 818, the maintenance carrier is returned to storage via the auto-loader after completing a maintenance task. At step 820, a processor considers the current state of the returned maintenance carrier and determines if the maintenance carrier needs to be replaced, recharged or any payloads of a maintenance carrier replenished. These tasks can then be done automatically or a request can be placed to the operator to do any maintenance of the maintenance carrier manually. In some embodiment, one or more statuses of the maintenance carrier are monitored throughout the maintenance operation and reported to the operator, such as via a GUI at a terminal that reports statuses of the automation system.

The systems discussed herein can be managed by any suitable means, including one or more processors (e.g., a CPU, DSP, APU, GPU, single or multi-core processors, microcontrollers, etc., along with suitable memory and hardware) that may be local and dedicated to a module, shared by modules, part of a larger central controller system, or remote processors available via a network. The means could additionally, or alternatively, include dedicated circuits (e.g., ASICs, FPGAs, etc.) or other hardware suitable for creating an electrical output from sensor input. The processors or circuits can receive input about samples/payload and/or sample carriers in the queue from memory and/or sensors to determine any status information about a queue. These processors or circuits can direct the samples and carriers holding the samples via any suitable means, including electrical/mechanical mechanisms of the automation system or local module that operates under the control of, or in response to, the processors or circuits. It should be understood that the term processor could encompass single or multiple processors which may operate together or separately, and can include general purpose computers operating on a network or standing alone. In some embodiments, the electrical/mechanical mechanisms operate independently of the processors or circuits handling the queues, but the processors or circuits can send requests for motion via any suitable protocol, such as a wireless protocol, such as XBee, wired protocol, such as CAN, or other suitable means. The mechanism used to move samples and their carriers can be in any suitable form, including magnetic motion, linear motors, gears, friction surfaces, air, or pneumatic, hydraulic, or electromagnetic mechanisms. In some embodiments, the motive force is generated by the automation system, the local analyzer module, the sample carriers, or any combination thereof.

In embodiments where a carrier has some steering capability and can turn at a decision point without the assistance of the next internal switch, the carrier can engage its steering mechanism to direct it to the appropriate path upon approaching the decision point. After turning at the decision point (or proceeding without turning) a carrier returns to step 504 to determine its next trajectory.

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. An automation system comprising:
   a track;
   a plurality of maintenance carriers; and an auto-loader for selectively deploying one or more or the plurality of maintenance carriers on the track,
wherein the auto-loader selects a maintenance carrier in response to a detected condition of the track.

2. The automation system of claim 1, further comprising a plurality of sample carriers that traverse the track.

3. The automation system of claim 1, wherein the auto-loader comprises a robot arm.

4. The automation system of claim 1, wherein the plurality of maintenance carriers comprises a plurality of types of maintenance carriers.

5. The automation system of claim 1, further comprising a storage rack that stores the plurality of maintenance carriers.

6. The automation system of claim 5, wherein the storage rack is configured to recharge the plurality of maintenance carriers.

7. The automation system of claim 1, wherein the auto-loader is configured to install a maintenance cartridge in one or more of the plurality of maintenance carriers.

8. The automation system of claim 1, wherein the auto-loader is configured to replenish a fluid in one or more of the plurality of maintenance carriers.

9. A method for performing maintenance to an analyzer comprising the steps of:
determining a maintenance operation to perform;
automatically selecting a maintenance carrier to perform the maintenance operation;
under the control of a processor, automatically deploying the maintenance carrier onto a track;
performing the maintenance operation using the maintenance carrier;
returning the maintenance carrier to a storage or waste location;
determining a status of a fluid in the maintenance carrier; and
replacing a maintenance cartridge in the maintenance carrier if the fluid level is low.

10. The method of claim 9, wherein the step of determining a maintenance operation to perform occurs in response to an explicit request by an operator.

11. The method of claim 9, wherein the step of determining a maintenance operation to perform occurs in response to detecting an error.

12. The method of claim 9, wherein the step of determining a maintenance operation to perform occurs at a pre-scheduled time.

13. The method of claim 9, further comprising refilling the fluid in the maintenance carrier if the fluid level is low.

14. The method of claim 9, further comprising the step of recharging the maintenance carrier when it is in the storage location.

15. The method of claim 9, further comprising monitoring at least one status of the maintenance carrier and reporting that status to an operator.

16. The method of claim 9, wherein the maintenance carrier is selected from a plurality of maintenance carriers in the storage location.

17. An auto-loader for use with an automation system comprising:
a storage area configured to hold a plurality of maintenance carriers; and
a robot arm configured to selectively load and unload at least one of the plurality of maintenance carriers with respect to at least one automation track, wherein the robot arm is further configured to move the at least one of the plurality of maintenance carriers responsive to a processor in communication with an analyzer,
wherein the storage area is configured to recharge at least one of the maintenance carriers.

18. The auto-loader of claim 17, wherein the storage area is configured to install a maintenance cartridge in one or more of the plurality of maintenance carriers.

* * * * *